(12) United States Patent
Moran et al.

(10) Patent No.: US 9,918,443 B2
(45) Date of Patent: Mar. 20, 2018

(54) HYBRID SWEET CORN PLANT HMX4370BS

(71) Applicant: HM.Clause, Inc., Davis, CA (US)

(72) Inventors: Terrance Moran, Naples, FL (US);
Patrick Mosely, Middleton, WI (US);
Edward Snyder, Madison, WI (US);
Kenneth Christensen, Nampa, ID (US)

(73) Assignee: HM.CLAUSE, INC., Davis, CA (US)

( * ) Notice: Subject to any disclaimer, the term of this patent is extended or adjusted under 35 U.S.C. 154(b) by 162 days.

(21) Appl. No.: 14/978,297

(22) Filed: Dec. 22, 2015

(65) Prior Publication Data
US 2016/0212963 A1  Jul. 28, 2016

Related U.S. Application Data

(60) Provisional application No. 62/095,389, filed on Dec. 22, 2014.

(51) Int. Cl.
*A01H 5/00* (2006.01)
*C12N 15/82* (2006.01)
*A01H 5/10* (2018.01)

(52) U.S. Cl.
CPC ........... *A01H 5/10* (2013.01); *C12N 15/8249* (2013.01)

(58) Field of Classification Search
None
See application file for complete search history.

(56) References Cited

U.S. PATENT DOCUMENTS 8,581,078 B2 * 11/2013 Hellewell ............... A01H 5/10
435/410

* cited by examiner

*Primary Examiner* — Vinod Kumar
(74) *Attorney, Agent, or Firm* — Cooley LLP

(57) ABSTRACT

A novel sweet corn hybrid plant, designated HMX4370BS is disclosed. The invention relates to the seeds of sweet corn hybrid HMX4370BS, to the plants and plant parts of sweet corn hybrid HMX4370BS, and to methods for producing a sweet corn plant by crossing the sweet corn hybrid HMX4370BS with itself or another sweet corn plant. The invention further relates to methods for producing a sweet corn plant containing in its genetic material one or more transgenes and to the transgenic plants produced by that method and to methods for producing other sweet corn plants derived from the sweet corn hybrid plant HMX4370BS.

24 Claims, No Drawings

HYBRID SWEET CORN PLANT HMX4370BS

CROSS-REFERENCE TO RELATED APPLICATIONS

The present application claims priority to, and the benefit of U.S. Provisional Patent Application No. 62/095,389, filed Dec. 22 2014, which is herein incorporated by reference in its entirety for all purposes.

FIELD OF THE INVENTION

The present invention relates to the field of agriculture, to new and distinctive hybrid sweet corn plants, such as hybrid plants designated HMX4366YS and/or HMX4370BS and to methods of making and using such hybrids.

BACKGROUND OF THE INVENTION

The following description includes information that may be useful in understanding the present invention. It is not an admission that any of the information provided herein is prior art or relevant to the presently claimed inventions, or that any publication specifically or implicitly referenced is prior art.

Sweet Corn is an important and valuable vegetable crop. Thus, a continuing goal of plant breeders is to develop stable, high yielding sweet corn hybrids that are agronomically sound or unique. The reasons for this goal are to maximize the amount of ears or kernels produced on the land used (yield) as well as to improve the plant, the ears husks, eating qualities and/or kernels agronomic qualities. To accomplish this goal, the sweet corn breeder must select and develop sweet corn plants that have the traits that result in superior parental lines that combine to produce superior hybrids.

SUMMARY OF THE INVENTION

The following embodiments and aspects thereof are described in conjunction with systems, tools and methods which are meant to be exemplary, not limiting in scope.

In various embodiments, one or more of the above-described problems have been reduced or eliminated, while other embodiments are directed to other improvements.

According to the invention, there are provided novel sweet corn hybrids, designated HMX4366YS and/or HMX4370BS. This invention thus relates to the seeds of sweet corn hybrid designated HMX4366YS and/or HMX4370BS, to the plants or parts thereof of sweet corn hybrid designated HMX4366YS and/or HMX4370BS, to plants or parts thereof consisting essentially of the phenotypic and morphological characteristics of sweet corn hybrid designated HMX4366YS and/or HMX4370BS, and/or having all the physiological and morphological characteristics of sweet corn hybrid designated HMX4366YS and/or HMX4370BS, and/or having one or more or all of the characteristics of sweet corn hybrid designated HMX4366YS and/or HMX4370BS listed in Tables 1 to 2 including, but not limited to, as determined at the 5% significance level when grown in the same environmental condition, and/or having the physiological and morphological characteristics of sweet corn hybrid designated HMX4366YS and/or HMX4370BS listed in Tables 1 to 2 including, but not limited to, as determined at the 5% significance level when grown in the same environmental condition. The invention also relates to variants, mutants and trivial modifications of the seed or plant of sweet corn hybrid designated HMX4366YS and/or HMX4370BS.

Plant parts of the sweet corn hybrid plant of the present invention are also provided, such as ear, kernel, leaf, flower, cell, pollen, stalk, roots, anther or ovule obtained from the hybrid plant. The present invention provides ears and kernels of the sweet corn hybrid of the present invention. Such ears and kernels could be used as fresh products for consumption or in processes resulting in processed products such as prepared kernels, canned kernels, freeze dried or frozen kernels and the like. All such products are part of the present invention.

The plants and seeds of the present invention include those that may be of an essentially derived variety as defined in section 41(3) of the Plant Variety Protection Act of The United States of America, e.g., a variety that is predominantly derived from sweet corn hybrid designated HMX4366YS and/or HMX4370BS or from a variety that i) is predominantly derived from sweet corn hybrid designated HMX4366YS and/or HMX4370BS, while retaining the expression of the essential characteristics that result from the genotype or combination of genotypes of sweet corn hybrid designated HMX4366YS and/or HMX4370BS; ii) is clearly distinguishable from sweet corn hybrid designated HMX4366YS and/or HMX4370BS; and iii) except for differences that result from the act of derivation, conforms to the initial variety in the expression of the essential characteristics that result from the genotype or combination of genotypes of the initial variety.

In another aspect, the present invention provides regenerable cells. In some embodiments, the regenerable cells are for use in tissue culture of sweet corn hybrid designated HMX4366YS and/or HMX4370BS. In some embodiments, the tissue culture is capable of regenerating plants consisting essentially of the phenotypic and morphological characteristics of sweet corn hybrid designated HMX4366YS and/or HMX4370BS, and/or having all the phenotypic and morphological characteristics of sweet corn hybrid designated HMX4366YS and/or HMX4370BS, and/or having the physiological and morphological characteristics of sweet corn hybrid designated HMX4366YS and/or HMX4370BS, and/or having the characteristics of sweet corn hybrid designated HMX4366YS and/or HMX4370BS. In some embodiments, the plant parts and cells used to produce such tissue cultures will be embryos, meristematic cells, seeds, callus, pollen, leaves, anthers, pistils, roots, root tips, stems, petioles, kernels cotyledons, hypocotyls, ovaries, seed coat, silks, cobs, husks, stalks, endosperm, flowers, axillary buds or the like. Protoplasts produced from such tissue culture are also included in the present invention. The sweet corn shoots, roots and whole plants regenerated from the tissue culture, as well as the ears and kernels produced by said regenerated plants are also part of the invention. In some embodiments, the whole plants regenerated from the tissue culture have one, more than one, or all of the physiological and morphological characteristics of sweet corn hybrid designated HMX4366YS and/or HMX4370BS listed in Tables 1 to 2.

The invention also discloses methods for vegetatively propagating a plant of the present invention. In some embodiments, the methods comprise collecting a part of a sweet corn hybrid designated HMX4366YS and/or HMX4370BS and regenerating a plant from said part. In some embodiments, the part can be for example a stem cutting that is rooted into an appropriate medium according to techniques known by the one skilled in the art. Plants, part parts and fruits thereof produced by such methods are also included in the present invention. In another aspect, the plants, ears and kernels thereof produced by such methods consist essentially of the phenotypic and morphological characteristics of sweet corn hybrid designated HMX4366YS and/or HMX4370BS, and/or having all the phenotypic and morphological characteristics of sweet corn hybrid designated HMX4366YS and/or HMX4370BS, and/or having the physiological and morphological characteristics of sweet corn hybrid designated HMX4366YS and/or HMX4370BS, and/or having the characteristics of sweet corn hybrid designated HMX4366YS and/or HMX4370BS. In some embodiments, plants produced by such methods consist of one, more than one, or all phenotypic and morphological characteristics of sweet corn hybrid designated HMX4366YS and/or HMX4370BS listed in Tables 1 to 2. Further included in the invention are methods for producing ears and kernels from the sweet corn hybrid designated HMX4366YS and/or HMX4370BS. In some embodiments, the methods comprise growing a sweet corn hybrid designated HMX4366YS and/or HMX4370BS to produce sweet corn ears and kernels. In some embodiments, the methods further comprise harvesting the sweet corn ears. Such ears and their kernels are part of the present invention.

Also included in this invention are methods for producing a sweet corn plant. In some embodiments, the sweet corn plant is produced by crossing the sweet corn hybrid designated HMX4366YS and/or HMX4370BS with itself or another sweet corn plant. In some embodiments, the other plant can be a sweet corn plant. In some embodiments, the other plant can be a sweet corn hybrid or line. When crossed with an inbred line, in some embodiments, a "three-way cross" is produced. When crossed with itself or with another, different sweet corn hybrid, in some embodiments, a "four-way" cross is produced. Such three and four-way hybrid seeds and plants produced by growing said three and four-way hybrid seeds are included in the present invention. Methods for producing a three and four-way sweet corn hybrid seed comprising crossing sweet corn hybrid designated HMX4366YS and/or HMX4370BS sweet corn plant with a different sweet corn line or hybrid and harvesting the resultant sweet corn hybrid seed are also part of the invention. The sweet corn hybrid seeds produced by the method comprising crossing sweet corn hybrid designated HMX4366YS and/or HMX4370BS sweet corn plant with a different sweet corn plant and harvesting the resultant sweet corn hybrid seed are included in the invention, as are included the sweet corn hybrid plant or parts thereof and seeds produced by said grown sweet corn hybrid plants.

Further included in the invention are methods for producing sweet corn seeds and plants made thereof. In some embodiments, the methods comprise self-pollinating the sweet corn hybrid designated HMX4366YS and/or HMX4370BS and harvesting the resultant seeds. Sweet corn seeds produced by such method are also part of the invention.

In another embodiment, this invention relates to methods for producing a sweet corn hybrid designated HMX4366YS and/or HMX4370BS from a collection of seeds. In some embodiments, the collection contains both seeds of inbred parent lines of sweet corn hybrid designated HMX4366YS and/or HMX4370BS and hybrid seeds of HMX4366YS and/or HMX4370BS. Such a collection of seeds might be a commercial bag of seeds. In some embodiments, said methods comprise planting the collection of seeds. When planted, the collection of seeds will produce inbred parent lines of sweet corn hybrid and hybrid plants from the hybrid seeds of HMX4366YS and/or HMX4370BS. In some embodiments, said inbred parent lines of sweet corn hybrid designated HMX4366YS and/or HMX4370BS plants are identified as having a decreased vigor compared to the other plants (i.e., hybrid plants) grown from the collection of seeds. In some embodiments, said decreased vigor is due to the inbreeding depression effect and can be identified for example by a less vigorous appearance for vegetative and/or reproductive characteristics including a shorter plant height, small ear size, ear and kernel shape, ear color or other characteristics. In some embodiments, seeds of the inbred parent lines of the sweet corn hybrid HMX4366YS and/or HMX4370BS are collected, if new inbred plants thereof are grown and crossed in a controlled manner with each other, the sweet corn hybrid HMX4366YS and/or HMX4370BS will be recreated.

This invention also relates to methods for producing other sweet corn plants derived from sweet corn hybrid HMX4366YS and/or HMX4370BS and to the sweet corn plants derived by the use of those methods.

In some embodiments, such methods for producing a sweet corn plant derived from the hybrid variety HMX4366YS and/or HMX4370BS comprise (a) self-pollinating the sweet corn hybrid HMX4366YS and/or HMX4370BS plant at least once to produce a progeny plant derived from sweet corn hybrid HMX4366YS and/or HMX4370BS; In some embodiments, the methods further comprise (b) crossing the progeny plant derived from sweet corn hybrid HMX4366YS and/or HMX4370BS with itself or a second corn plant to produce a seed of a progeny plant of a subsequent generation. In some embodiments, the methods further comprise (c) growing the progeny plant of the subsequent generation In some embodiments, the methods further comprise (d) crossing the progeny plant of the subsequent generation with itself or a second corn plant to produce a sweet corn plant further derived from the sweet corn hybrid HMX4366YS and/or HMX4370BS. In further embodiments, steps (b), (c) and/or (d) are repeated for at least 1, 2, 3, 4, 5, 6, 7, 8, or more generations to produce a sweet corn plant derived from the sweet corn hybrid variety HMX4366YS and/or HMX4370BS. In some embodiments, within each crossing cycle, the second plant is the same plant as the second plant in the last crossing cycle. In some embodiments, within each crossing cycle, the second plant is different from the second plant in the last crossing cycle. In some embodiments, within each crossing cycle, the second corn plant is a sweet corn plant.

Another method for producing a sweet corn plant derived from the hybrid variety HMX4366YS and/or HMX4370BS, comprises the steps of: (a) crossing the sweet corn hybrid HMX4366YS and/or HMX4370BS plant with a second corn plant to produce a progeny plant derived from sweet corn hybrid HMX4366YS and/or HMX4370BS. In some embodiments, the methods further comprise (b) crossing the progeny plant derived from sweet corn hybrid HMX4366YS and/or HMX4370BS with itself or a second sweet corn plant to produce a seed of a progeny plant of a subsequent generation; In some embodiments, the methods further comprise (c) growing the progeny plant of the subsequent generation; In some embodiments, the methods further comprise (d) crossing the progeny plant of the subsequent generation with itself or a second corn plant to produce a sweet corn plant derived from the sweet corn hybrid variety HMX4366YS and/or HMX4370BS. In a further embodiment, steps (b), (c) and/or (d) are repeated for at least 1, 2, 3, 4, 5, 6, 7, 8, or more generations to produce a sweet corn plant derived from the sweet corn hybrid variety HMX4366YS and/or HMX4370BS. In some embodiments, within each crossing cycle, the second plant is the same plant as the second plant in the last crossing cycle. In some embodiments, within each crossing cycle, the second plant is different from the second plant in the last crossing cycle. In some embodiments, within each crossing cycle, the second corn plant is a sweet corn plant.

More specifically, the invention comprises methods for producing a male sterile sweet corn plant, an herbicide resistant sweet corn plant, an insect resistant sweet corn plant, a disease resistant sweet corn plant, a water-stress-tolerant plant, a heat stress tolerant plants, an improved shelf life sweet corn plant, a sweet corn plant with increased sweetness and flavor, a sweet corn plant with increased sugar content, a sweet corn plant with enhanced nutritional quality, a sweet corn plant with improved nutritional use efficiency, a sweet corn plant with delayed senescence or controlled ripening and/or plants with improved salt tolerance. In some embodiments, said methods comprise transforming the hybrid designated HMX4366YS and/or HMX4370BS sweet corn plant with nucleic acid molecules that confer male sterility, herbicide resistance, insect resistance, disease resistance, water-stress tolerance, heat stress tolerance, increased shelf life, increased sweetness and flavor, enhanced nutritional quality, improved nutritional use efficiency, increased sugar content, delayed senescence or controlled ripening and/or improved salt tolerance, respectively. The transformed sweet corn plants or parts thereof, obtained from the provided methods, including for example a male sterile sweet corn plant, an herbicide resistant sweet corn plant, an insect resistant sweet corn plant, a disease resistant sweet corn plant, a sweet corn with water stress tolerance, a sweet corn plant with heat stress tolerance, a sweet corn plant with increased sweetness and flavor, a sweet corn plant with increased sugar content, a sweet corn with enhanced nutritional quality, a sweet corn plant with improved nutritional use efficiency, a sweet corn plant with delayed senescence or controlled ripening or a sweet corn plant with improved salt tolerance are included in the present invention. Plants may display one or more of the above listed traits. For the present invention and the skilled artisan, disease is understood to include, but not limited to fungal diseases, viral diseases, bacterial diseases, mycoplasm diseases, or other plant pathogenic diseases and a disease resistant plant will encompass a plant resistant to fungal, viral, bacterial, mycoplasm, and other plant pathogens.

In another aspect, the present invention provides methods of introducing one or more desired trait(s) into the sweet corn hybrid HMX4366YS and/or HMX4370BS and plants or seeds obtained from such methods. The desired trait(s) may be, but not exclusively, a single gene. In some embodiments, the gene is a dominant allele. In some embodiments, the gene is a partially dominant allele. In some embodiments, the gene is a recessive allele. In some embodiments, the transferred gene or genes will confer such traits including, but not limited to, male sterility, herbicide resistance, insect resistance, resistance for bacterial, fungal, mycoplasma or viral disease, improved shelf life, water-stress tolerance, delayed senescence or controlled ripening, enhanced nutritional quality such as increased sugar content or increased sweetness, increased texture, flavor and aroma, enhanced plant quality such as improved drought or salt tolerance, improved standability, enhanced plant vigor or enhanced nutritionally quality, improved husk length, protection or color, ear shape, fill, length or diameter, kernel color, refinement or depth, lodging resistance, yield and recovery. The gene or genes may be naturally occurring or corn gene(s), mutant(s) or transgene(s) introduced through genetic engineering techniques. In some embodiments, the methods for introducing the desired trait(s) comprise backcrossing process making use of a series of backcrosses to at least one of the parent lines of sweet corn hybrid HMX4366YS and/or HMX4370BS during which the desired trait(s) is maintained by selection. The single gene conversion plants that can be obtained by the methods are included in the present invention.

When using a transgene, in some embodiments, the trait is generally not incorporated into each newly developed hybrid such as HMX4366YS and/or HMX4370BS by direct transformation. Rather, the more typical method used by breeders of ordinary skill in the art to incorporate the transgene is to take a line already carrying the transgene and to use such line as a donor line to transfer the transgene into one or more of the parents of the newly developed hybrid. The same would apply for a naturally occurring trait or one arising from spontaneous or induced mutations. In some embodiments, the backcross breeding process comprises (a) crossing one of the parental inbred line plants of HMX4366YS and/or HMX4370BS with plants of another line that comprise the desired trait(s) to produce F1 progeny plants; In some embodiments, the process further comprises (b) selecting the F1 progeny plants that have the desired trait(s); In some embodiments, the process further comprises (c) crossing the selected F1 progeny plants with the parental inbred sweet corn lines of hybrid HMX4366YS and/or HMX4370BS plants to produce backcross progeny plants; In some embodiments, the process further comprises (d) selecting for backcross progeny plants that have the desired trait(s) and physiological and morphological characteristics of the sweet corn parental inbred line of sweet corn hybrid HMX4366YS and/or HMX4370BS to produce selected backcross progeny plants; In some embodiments, the process further comprises (e) repeating steps (c) and (d) one, two, three, four, five six, seven, eight, nine or more times in succession to produce selected, second, third, fourth, fifth, sixth, seventh, eighth, ninth or higher backcross progeny plants that have the desired trait(s) and consist essentially of the phenotypic and morphological characteristics of the parental inbred sweet corn line of sweet corn HMX4366YS and/or HMX4370BS, and/or have all the phenotypic and morphological characteristics of the parental sweet corn inbred line of sweet corn hybrid HMX4366YS and/or HMX4370BS, and/or the physiological and morphological characteristics of the parental inbred sweet corn line of sweet corn hybrid HMX4366YS and/or HMX4370BS as determined in Tables 1 to 2, including but not limited to, at a 5% significance level when grown in the same environmental conditions. The sweet corn plants or seed produced by the methods are also part of the invention, as are the sweet corn hybrid HMX4366YS and/or HMX4370BS plants that comprised the desired trait. Backcrossing breeding methods, well known to one skilled in the art of plant breeding will be further developed in subsequent parts of the specification.

In an embodiment of this invention is a method of making a backcross conversion of sweet corn hybrid HMX4366YS and/or HMX4370BS. In some embodiments, the method comprises crossing one of the parental sweet corn inbred line plants of hybrid HMX4366YS and/or HMX4370BS with a donor plant comprising a mutant gene(s), a naturally occurring gene(s), or transgene(s) conferring one or more desired trait to produce F1 progeny plants; In some embodiments, the method further comprises selecting the F1 progeny plant comprising the naturally occurring gene(s), mutant gene(s) or transgene(s) conferring the one or more desired trait; In some embodiments, the method further comprises backcrossing the selected progeny plant to the parental sweet corn inbred line plants of hybrid HMX4366YS and/or HMX4370BS. This method may further comprise the step of obtaining a molecular marker profile of the parental sweet corn inbred line plants of hybrid HMX4366YS and/or HMX4370BS and using the molecular marker profile to select for the progeny plant with the desired trait and the molecular marker profile of the parental sweet corn inbred line plants of hybrid HMX4366YS and/or HMX4370BS. In some embodiments, this method further comprises crossing the backcross progeny plant HMX4366YS and/or HMX4370BS containing the naturally occurring gene(s), the mutant gene(s) or the transgene(s) conferring the one or more desired trait with the second parental inbred sweet corn line plants of sweet corn hybrid HMX4366YS and/or HMX4370BS in order to produce the sweet corn hybrid HMX4366YS and/or HMX4370BS comprising the naturally occurring gene(s), the mutant gene(s) or transgene(s) conferring the one or more desired trait. The plants or parts thereof produced by such methods are also part of the present invention.

In some embodiments of the invention, the number of loci that may be backcrossed into the parental sweet corn inbred line of hybrid HMX4366YS and/or HMX4370BS is at least 1, 2, 3, 4, 5, or more. A single locus may contain several genes and/or transgenes, such as a transgene for disease resistance that, in the same expression vector, also contains a transgene for herbicide resistance. The gene for herbicide resistance may be used as a selectable marker and/or as a phenotypic trait. A single locus conversion of site specific integration system allows for the integration of multiple genes at the converted locus. A single locus conversion also allows for making one or more site specific changes to the plant genome. In some embodiments, the single locus conversion is performed by genome editing, a.k.a. genome editing with engineered nucleases (GEEN). In some embodiments, the genome editing comprises using one or more engineered nucleases. In some embodiments, the engineered nucleases include, but are not limited to Zinc finger nucleases (ZFNs), Transcription Activator-Like Effector Nucleases (TALEN5), the CRISPR/Cas system, and engineered meganuclease re-engineered homing endonucleases. In some embodiments, the single locus conversion changes one or several nucleic acids of the plant genome.

The invention further provides methods for developing sweet corn plants in a sweet corn plant breeding program using plant breeding techniques including but not limited to, recurrent selection, backcrossing, pedigree breeding, genomic selection, molecular marker (Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), and Simple Sequence Repeats (SSRs) which are also referred to as Microsatellites, Single Nucleotide Polymorphism (SNP), etc.) enhanced selection, genetic marker enhanced selection and transformation. Seeds, sweet corn plants, and parts thereof produced by such breeding methods are also part of the invention.

The invention also relates to variants, mutants and trivial modifications of the seed or plant of the sweet corn hybrid HMX4366YS and/or HMX4370BS or inbred parental lines thereof. Variants, mutants and trivial modifications of the seed or plant of sweet corn hybrid HMX4366YS and/or HMX4370BS or inbred parental lines thereof can be generated by methods available to one skilled in the art, including but not limited to, mutagenesis (e.g., chemical mutagenesis, radiation mutagenesis, transposon mutagenesis, insertional mutagenesis, signature tagged mutagenesis, site-directed mutagenesis, and natural mutagenesis), knock-outs/knock-ins, antisense and RNA interference. For more information of mutagenesis in plants, such as agents, protocols, see Acquaah et al. (Principles of plant genetics and breeding, Wiley-Blackwell, 2007, ISBN 1405136464, 9781405136464, which is herein incorporated by reference in its entity).

The invention also relates to a mutagenized population of the sweet corn hybrid HMX4366YS and/or HMX4370BS and methods of using such populations. In some embodiments, the mutagenized population can be used in screening for new sweet corn plants which comprise one or more or all of the morphological and physiological characteristics of sweet corn hybrid HMX4366YS and/or HMX4370BS. In some embodiments, the new sweet corn plants obtained from the screening process comprise all of the morphological and physiological characteristics of the sweet corn hybrid HMX4366YS and/or HMX4370BS, and one or more additional or different morphological and physiological characteristics that the sweet corn hybrid HMX4366YS and/or HMX4370BS does not have.

This invention also is directed to methods for producing a sweet corn plant by crossing a first parent sweet corn plant with a second parent sweet corn plant wherein either the first or second parent sweet corn plant is a sweet corn hybrid plant of HMX4366YS and/or HMX4370BS. Further, both first and second parent sweet corn plants can come from the sweet corn hybrid plant HMX4366YS and/or HMX4370BS. Further, the sweet corn hybrid plant HMX4366YS and/or HMX4370BS can be self-pollinated i.e. the pollen of a sweet corn hybrid plant HMX4366YS and/or HMX4370BS can pollinate the ovule of the same sweet corn hybrid plant HMX4366YS and/or HMX4370BS. When crossed with another sweet corn plant, a hybrid seed is produced. Such methods of hybridization and self-pollination are well known to those skilled in the art of breeding.

An inbred sweet corn line such as one of the parental lines of sweet corn hybrid HMX4366YS and/or HMX4370BS has been produced through several cycles of self-pollination and is therefore to be considered as a homozygous line. An inbred line can also be produced though the dihaploid system which involves doubling the chromosomes from a haploid plant or embryo thus resulting in an inbred line that is genetically stable (homozygous) and can be reproduced without altering the inbred line: Haploid plants could be obtained from haploid embryos that might be produced from microspores, pollen, anther cultures or ovary cultures or spontaneous haploidy. The haploid embryos may then be doubled by chemical treatments such as by colchicine or be doubled autonomously. The haploid embryos may also be grown into haploid plants and treated to induce the chromosome doubling. In either case, fertile homozygous plants are obtained. A hybrid variety is classically created through the fertilization of an ovule from an inbred parental line by the pollen of another, different inbred parental line. Due to the homozygous state of the inbred line, the produced gametes carry a copy of each parental chromosome. As both the ovule and the pollen bring a copy of the arrangement and organization of the genes present in the parental lines, the genome of each parental line is present in the resulting F1 hybrid, theoretically in the arrangement and organization created by the plant breeder in the original parental line.

As long as the homozygosity of the parental lines is maintained, the resulting hybrid cross shall be stable. The F1 hybrid is then a combination of phenotypic characteristics issued from two arrangement and organization of genes, both created by a person skilled in the art through the breeding process.

Still further, this invention also is directed to methods for producing a sweet corn plant derived from sweet corn hybrid HMX4366YS and/or HMX4370BS- by crossing sweet corn hybrid plant HMX4366YS and/or HMX4370BS with a second corn plant. In some embodiments, the methods further comprise obtaining a progeny seed from the cross. In some embodiments, the methods further comprise growing the progeny seed, and possibly repeating the crossing and growing steps with the sweet corn hybrid plant HMX4366YS and/or HMX4370BS-derived plant from 0 to 7 or more times. In some embodiments, the second corn plant is a sweet corn plant. Thus, any such methods using the sweet corn hybrid plant HMX4366YS and/or HMX4370BS are part of this invention: selfing, backcrosses, hybrid production, crosses to populations, and the like. All plants produced using sweet corn hybrid plant HMX4366YS and/or HMX4370BS as a parent are within the scope of this invention, including plants derived from sweet corn hybrid plant HMX4366YS and/or HMX4370BS. In some embodiments, such plants have one or more or all physiological and morphological characteristics of the sweet corn hybrid plant HMX4366YS and/or HMX4370BS. In some embodiments, such plants might exhibit additional and desired characteristics or traits such as high seed yield, high seed germination, seedling vigor, early maturity, high yield, disease tolerance or resistance, lodging resistance and adaptability for soil and climate conditions. Consumer-driven traits, such as a preference for a given ear size, kernels color, kernels texture, kernels taste, kernels firmness, kernels sugar content are other traits that may be incorporated into new sweet corn plants developed by this invention.

A sweet corn plant can also be propagated vegetatively. A part of the plant, for example a shoot tissue, is collected, and a new plant is obtained from the part. Such part typically comprises an apical meristem of the plant. The collected part is transferred to a medium allowing development of a plantlet, including for example rooting or development of shoots, or is grafted onto a sweet corn plant or a rootstock prepared to support growth of shoot tissue. This is achieved using methods well-known in the art. Accordingly, in one embodiment, a method of vegetatively propagating a plant of the present invention comprises collecting a part of a plant according to the present invention, e.g. a shoot tissue, and obtaining a plantlet from said part. In one embodiment, a method of vegetatively propagating a plant of the present invention comprises: a) collecting tissue of a plant of the present invention; b) rooting said proliferated shoots to obtain rooted plantlets. In one embodiment, a method of vegetatively propagating a plant of the present invention comprises: a) collecting tissue of a plant of the present invention; b) cultivating said tissue to obtain proliferated shoots; c) rooting said proliferated shoots to obtain rooted plantlets. In one embodiment, such method further comprises growing a plant from said plantlets. In one embodiment, an ear is harvested from said plant. In one embodiment, the ear and/or its kernels is processed into products such as canned kernels, freeze dried or frozen kernels, fresh or prepared ear or kernels and the like.

In some embodiments, the present invention teaches a seed of sweet corn hybrid designated HMX4370BS, wherein a representative sample of seed of said hybrid is deposited under NCIMB No. 42798.

In some embodiments, the present invention teaches a sweet corn plant, or a part thereof, produced by growing the deposited HMX4366YS and/or HMX4370BS seed.

In some embodiments, the present invention teaches sweet corn plant parts, wherein the sweet corn part includes, but is not limited to, a leaf, a flower, a kernel, an ear, an ovule, pollen, a cell.

In some embodiments, the present invention teaches a sweet corn plant, or a part thereof, having all of the characteristics of hybrid HMX4366YS and/or HMX4370BS as listed in Tables 1 to 2 of this application.

In some embodiments, the present invention teaches a sweet corn plant, or a part thereof, having all of the physiological and morphological characteristics of hybrid HMX4370BS, wherein a representative sample of seed of said hybrid was deposited under NCIMB No. 42798.

In some embodiments, the present invention teaches a tissue culture of regenerable cells produced from the plant or plant part grown from the deposited HMX4366YS and/or HMX4370BS seed, wherein cells of the tissue culture are produced from a plant part selected from the group consisting of protoplasts, embryos, meristematic cells, callus, pollen, ovules, flowers, seeds, leaves, roots, root tips, anthers, stems, petioles, fruits, axillary buds, cotyledons and hypocotyls. In some embodiments, the plant part includes protoplasts produced from a plant grown from the deposited HMX4366YS and/or HMX4370BS seed.

In some embodiments, the present invention teaches a sweet corn plant regenerated from the tissue culture from a plant grown from the deposited HMX4370BS seed, said plant having the characteristics of hybrid HMX4370BS, wherein a representative sample of seed of said hybrid is deposited under NCIMB No. 42798.

In some embodiments, the present invention teaches a sweet corn ear and kernels produced from the plant grown from the deposited HMX4366YS and/or HMX4370BS seed.

In some embodiments, methods of producing said sweet corn ear comprise a) growing the sweet corn plant from deposited HMX4366YS and/or HMX4370BS seed to produce a sweet corn ear, and b) harvesting said sweet corn ear. In some embodiments, the present invention also teaches a sweet corn ear produced by the method of producing sweet corn ears and/or kernels as described above.

In some embodiments, the present invention teaches methods for producing a sweet corn seed comprising crossing a first parent sweet corn plant with a second parent sweet corn plant and harvesting the resultant sweet corn seed, wherein said first parent sweet corn plant and/or second parent sweet corn plant is the sweet corn plant produced from the deposited HMX4366YS and/or HMX4370BS seed or a sweet corn plant having all of the characteristics of sweet corn hybrid HMX4366YS and/or HMX4370BS as listed in Tables 1 to 2.

In some embodiments, the present invention teaches methods for producing a sweet corn seed comprising self-pollinating the sweet corn plant grown from the deposited HMX4366YS and/or HMX4370BS seed and harvesting the resultant sweet corn seed.

In some embodiments, the present invention teaches the seed produced by any of the above described methods.

In some embodiments, the present invention teaches methods of vegetatively propagating the sweet corn plant grown from the deposited HMX4366YS and/or HMX4370BS seed, said method comprising a) collecting part of a plant grown from the deposited HMX4366YS and/or HMX4370BS seed and b) regenerating a plant from said part.

In some embodiments, the method further comprises harvesting an ear and/or kernels from said vegetatively propagated plant.

In some embodiments, the present invention teaches the plant and the ear and/or kernels of plants vegetatively propagated from plant parts of plants grown from the deposited HMX4366YS and/or HMX4370BS seed.

In some embodiments, the present invention teaches methods of producing a sweet corn plant derived from the hybrid variety HMX4366YS and/or HMX4370BS, the methods comprise: (a) self-pollinating the plant grown from the deposited HMX4366YS and/or HMX4370BS seed at least once to produce a progeny plant derived from sweet corn HMX4366YS and/or HMX4370BS; In some embodiments, the method further comprises (b) crossing the progeny plant derived from sweet corn HMX4366YS and/or HMX4370BS with itself or a second corn plant to produce a seed of a progeny plant of a subsequent generation; and; (c) growing the progeny plant of the subsequent generation from the seed, and crossing the progeny plant of the subsequent generation with itself or a second corn plant to produce a sweet corn plant derived from the sweet corn hybrid variety HMX4366YS and/or HMX4370BS. In some embodiments said methods further comprise the step of: (d) repeating steps b) or c) for at least 1, 2, 3, 4, 5, 6, 7, or more generation to produce a sweet corn plant derived from the sweet corn hybrid variety HMX4366YS and/or HMX4370BS. In some embodiments, the second corn plant is a sweet corn plant.

In some embodiments, the present invention teaches methods of producing a sweet corn plant derived from the hybrid variety HMX4366YS and/or HMX4370BS, the methods comprising: (a) crossing the plant grown from the deposited HMX4366YS and/or HMX4370BS seed with a second corn plant to produce a progeny plant derived from sweet corn HMX4366YS and/or HMX4370BS; In some embodiments, the method further comprises (b) crossing the progeny derived from sweet corn HMX4366YS and/or HMX4370BS with itself or a second sweet corn plant to produce a seed of a progeny plant of a subsequent generation; and; (c) growing the progeny plant of the subsequent generation from the seed; (d) crossing the progeny plant of the subsequent generation with itself or a second corn plant to produce a sweet corn plant derived from the sweet corn hybrid variety HMX4366YS and/or HMX4370BS. In some embodiments said methods further comprise the steps of: (e) repeating step (b), (c) and/or (d) for at least 1, 2, 3, 4, 5, 6, 7, or more generation to produce a sweet corn plant derived from the sweet corn hybrid variety HMX4366YS and/or HMX4370BS. In some embodiments, the second corn plant is a sweet corn plant In some embodiments, the present invention teaches methods for producing a transgenic sweet corn plant, the methods comprising crossing a first sweet corn plant grown from the deposited HMX4366YS and/or HMX4370BS seed with a second corn plant containing a transgene, wherein the transgene of said second corn plant is integrated into the genome of the sweet corn plant progeny resulting from said cross, and wherein the transgene confers said sweet corn plant progeny with at least one trait selected from the group consisting of male sterility, male fertility, herbicide resistance, insect resistance, disease resistance, water stress tolerance, heat stress tolerance, increased sweetness, increased sugar content, increased flavor, improved ripening control, improved shelf life, and improved salt tolerance when compared to plants not comprising such transgene. In some embodiments, the plant not comprising such transgene is a sweet corn hybrid HMX4366YS and/or HMX4370BS. In some embodiments, the second corn plant is a sweet corn plant.

In some embodiments, the present invention teaches methods for producing a transgenic sweet corn plant, the methods comprising transforming at least one transgene into a sweet corn hybrid HMX4370BS plant, or a plant part or a plant cell thereof or parental line used for producing the sweet corn hybrid plant HMX4370BS, a sample seed of said hybrid having been deposited under NCIMB No. 42798 thereby producing a transgenic sweet corn plant.

In some embodiments, the present invention teaches sweet corn plants and sweet corn ears and/or kernels produced by any of the above-described methods of producing transgenic sweet corn. Thus, in some embodiments, the present invention teaches a plant grown from the deposited HMX4366YS and/or HMX4370BS seed, further comprising a transgene. In some embodiments, said transgenic sweet corn plants comprise transgenes which confer said plant with a trait selected from the group consisting of male sterility, male fertility, herbicide resistance, insect resistance, disease resistance, water stress tolerance, heat stress tolerance, increased sweetness, increased sugar content, increased flavor, improved ripening control, improved shelf life, and improved salt tolerance when compared with plants not comprising such transgene In some embodiments, the plant not comprising such transgene is a sweet corn hybrid HMX4366YS and/or HMX4370BS.

In some embodiments, the present invention teaches plants grown from the deposited HMX4366YS and/or HMX4370BS seed wherein said plants comprise at least one single locus conversion. In some embodiments said single locus conversion confers said plants with a trait selected from the group consisting of male sterility, male fertility, herbicide resistance, insect resistance, disease resistance, increased sweetness, increased sugar content, increased flavor, water-stress tolerance, improved ripening control, improved shelf life, delayed senescence, enhanced nutritional quality such as increased sugar content or increased sweetness, increased texture, flavor and aroma, enhanced plant quality such as improved drought or salt tolerance, improved husk length, protection or color, ear shape, fill, length or diameter, kernel color, refinement or depth, lodging resistance, yield and recovery when compared to plants not comprising such single locus conversion. In some embodiments, the plant not comprising such single locus conversion is a sweet corn hybrid HMX4366YS and/or HMX4370BS In some embodiments, the at least one single locus conversion is an artificially mutated gene.

In addition to the exemplary aspects and embodiments described above, further aspects and embodiments will become apparent by study of the following descriptions.

DETAILED DESCRIPTION OF THE INVENTION

Definitions

In the description and tables that follow, a number of terms are used. In order to provide a clear and consistent understanding of the specification and claims, including the scope to be given such terms, the following definitions are provided:

Allele. An allele is any of one or more alternative forms of a gene which relate to one trait or characteristic. In a diploid cell or organism, the two alleles of a given gene occupy corresponding loci on a pair of homologous chromosomes.

Backcrossing. Backcrossing is a process in which a breeder repeatedly crosses hybrid progeny back to one of the parents, for example, a first generation hybrid $F_1$ with one of the parental genotype of the $F_1$ hybrid.

Collection of seeds. In the context of the present invention a collection of seeds is a grouping of seeds mainly containing similar kind of seeds, for example hybrid seeds having the inbred line of the invention as a parental line, but that may also contain, mixed together with this first kind of seeds, a second, different kind of seeds, of one of the inbred parent lines, for example the inbred line of the present invention. A commercial bag of hybrid seeds having the inbred line of the invention as a parental line and containing also the inbred line seeds of the invention would be, for example such a collection of seeds.

Daily heat unit value. The daily heat unit value is calculated as follows: (the maximum daily temperature+the minimum daily temperature)/2 minus 50. All temperatures are in degrees Fahrenheit. The maximum temperature threshold is 86 degrees, if temperatures exceed this, 86 is used. The minimum temperature threshold is 50 degrees, if temperatures go below this, 50 is used.

Decreased vigor. A plant having a decreased vigor in the present invention is a plant that, compared to other plants has a less vigorous appearance for vegetative and/or reproductive characteristics including shorter plant height, small ear size, ear and kernel shape, ear color or other characteristics Endosperm Type. Endosperm type refers to endosperm genes and other quality affecting modifiers and types such as starch, sugary alleles (su1, su2, etc.), sugary enhancer (se1) or extender, waxy, amylose extender, dull, brittle alleles (bt1, bt2, etc.) shrunken-2 (sh2) and other sh alleles, and any combination of these.

Enhanced nutritional quality. The nutritional quality of the sweet corn of the present invention can be enhanced by the introduction of several traits comprising a higher endosperm sugar content, increased sweetness, a thinner pericarp, various endosperm types or mutants. Examples of genes governing such traits are the "sugary" gene (su1), the "Sugary Enhancer" gene (se1); and the Shrunken-2" gene (sh2).

Essentially all the physiological and morphological characteristics. A plant having essentially all the physiological and morphological characteristics means a plant having the physiological and morphological characteristics of the recurrent parent, except for the characteristics derived from the converted gene.

Grafting. Grafting is the operation by which a rootstock is grafted with a scion. The primary motive for grafting is to avoid damages by soil-born pest and pathogens when genetic or chemical approaches for disease management are not available. Grafting a susceptible scion onto a resistant rootstock can provide a resistant cultivar without the need to breed the resistance into the cultivar. In addition, grafting may enhance tolerance to abiotic stress, increase yield and result in more efficient water and nutrient uses.

HTU. HTU is the summation of the daily heat unit value calculated from emergence to harvest.

Immunity to disease(s) and or insect(s). A sweet corn plant which is not subject to attack or infection by specific disease(s) and or insect(s) is considered immune.

Industrial usage. The industrial usage of the sweet corn of the present invention comprises the use of the corn ears or kernels for consumption, whether as fresh products or in canning or freezing industries.

Intermediate resistance to disease(s) and or insect(s). A sweet corn plant that restricts the growth and development of specific disease(s) and or insect(s), but may exhibit a greater range of symptoms or damage compared to high resistant plants. Intermediate resistant plants will usually show less severe symptoms or damage than susceptible plant varieties when grown under similar environmental conditions and/or specific disease(s) and or insect(s) pressure, but may have heavy damage under heavy pressure. Intermediate resistant sweet corn plants are not immune to the disease(s) and or insect(s).

Maturity. Maturity is the number of days from seeding to harvesting.

Moisture. The moisture is the actual percentage moisture of the grain at harvest.

Plant adaptability. A plant having good plant adaptability means a plant that will perform well in different growing conditions and seasons.

Plant Cell. Plant cell, as used herein includes plant cells whether isolated, in tissue culture or incorporated in a plant or plant part.

Plant Part. As used herein, the term plant includes plant cells, plant protoplasts, plant cell tissue cultures from which sweet corn plants can be regenerated, plant calli, plant clumps and plant cells that are intact in plants or parts of plants, such as embryos, pollen, ovules, flowers, seeds, ears, kernels, rootstock, scions, stems, roots, anthers, pistils, root tips, leaves, meristematic cells, axillary buds, hypocotyls cotyledons, ovaries, seed coat endosperm and the like.

Quantitative Trait Loci (QTL) Quantitative trait loci refer to genetic loci that control to some degree numerically representable traits that are usually continuously distributed.

Regeneration. Regeneration refers to the development of a plant from tissue culture.

Resistance to disease(s) and or insect(s). A sweet corn plant that restricts the growth and development of specific disease(s) and or insect(s) under normal disease(s) and or insect(s) attack pressure when compared to susceptible plants. These sweet corn plants can exhibit some symptoms or damage under heavy disease(s) and or insect(s) pressure. Resistant sweet corn plants are not immune to the disease(s) and or insect(s).

Root Lodging. The root lodging is the percentage of plants that root lodge; i.e., those that lean from the vertical axis at an approximate 30□ angle or greater would be counted as root lodged.

Rootstock. A rootstock is the lower part of a plant capable of receiving a scion in a grafting process.

Scion. A scion is the higher part of a plant capable of being grafted onto a rootstock in a grafting process.

Single gene converted (conversion). Single gene converted (conversion) plants refer to plants which are developed by a plant breeding technique called backcrossing wherein essentially all of the desired morphological and physiological characteristics of a plant are recovered in addition to the single gene transferred into the plant via the backcrossing technique or via genetic engineering.

Susceptible to disease(s) and or insect(s). A sweet corn plant that is susceptible to disease(s) and or insect(s) is defined as a sweet corn plant that has the inability to restrict the growth and development of specific disease(s) and or insect(s). Plants that are susceptible will show damage when infected and are more likely to have heavy damage under moderate levels of specific disease(s) and or insect(s).

Tolerance to abiotic stresses. A sweet corn plant that is tolerant to abiotic stresses has the ability to endure abiotic stress without serious consequences for growth, appearance and yield.

Uniformity. Uniformity, as used herein, describes the similarity between plants or plant characteristics which can be a described by qualitative or quantitative measurements.

Variety. A plant variety as used by one skilled in the art of plant breeding means a plant grouping within a single botanical taxon of the lowest known rank which can be defined by the expression of the characteristics resulting from a given genotype or combination of phenotypes, distinguished from any other plant grouping by the expression of at least one of the said characteristics and considered as a unit with regard to its suitability for being propagated unchanged (International convention for the protection of new varieties of plants).

Yield. The yield is the tons of green corn or green weight per acre, It can also be defined as the number of ears per acre or per plant.

Sweet Corn Plants

Sweet corn is a particular type of maize (*Zea mays*, often referred to as corn in the United States). Sweet corn naturally mutated from field corn, with origins that are traced back to the Native Americans. Sweet corn is harvested at an earlier maturity than field corn (before it is dry), for a different purpose, usually fresh produce, canning or freezing, for human consumption, or to be eaten fresh on the cob, steamed or grilled. It has been bred therefore to be qualitatively and quantitatively different from field corn in a number of respects.

Early varieties, including those used by Native Americans, were the result of the mutant su1 ("sugary") allele. The sweet corn (su1) mutation causes the endosperm (storage area) of the seed to accumulate about two times more sugar than field corn. Today many sweet corn (su1) varieties are available. They contain about 5-10% sugar by weight.

Supersweet corns are varieties of sweet corn which produce higher than normal levels of sugar, first recognized by University of Illinois at Urbana-Champaign professor John Laughnan. He was investigating two specific genes in sweet corn, one of which, the sh2 (shrunken2) gene caused the corn to shrivel when dry. After further investigation Laughnan discovered that the endosperm of sh2 sweet corn kernels store less starch and from 4 to 10 times more sugar than standard sugary sweet corn. Texture is crispy rather than creamy as with the standard and sugary enhanced varieties. Fresh market shelf life is extended due to the ability of the kernels to retain moisture and sweetness for longer periods of time. He published his findings in 1953, disclosing the advantages of growing supersweet sweet corn, but many corn breeders lacked enthusiasm for the new supersweet corn. Illinois Foundation Seeds Inc. was the first seed company to release a supersweet corn and it was called Illini Xtra-Sweet, but widespread use of supersweet hybrids did not occur until the early 1980s. The popularity of supersweet corn rose due to its long shelf life and higher sugar content when compared to conventional sweet corn. This has improved the viability and thus the long-distance shipping of sweet corn and has enabled manufacturers to can sweet corn without adding extra sugar.

The third gene mutation to be discovered is the se1 or "sugary enhanced" allele. Sugary enhancer corn results in slightly increased sugar levels and a more creamy texture due to increased levels of water soluble polysaccharides. Kernels are also generally more tender.

All of the alleles responsible for sweet corn are recessive, so it must be isolated from any field corn varieties that release pollen at the same time; the endosperm develops from genes from both parents, and heterozygous kernels will be tough and starchy. The se1 and su1 alleles do not need to be isolated from each other as the change in quality of the sugary enhancer hybrids will not be that dramatic. Supersweet varieties containing the sh2 allele must be grown in isolation from other varieties to avoid cross-pollination and resulting starchiness, either in space (various sources quote minimum isolation distances from 100 to 400 feet or 30 to 120 m) or in time (i.e., the supersweet corn does not pollinate at the same time as other corn in nearby fields).

Sweet corn hybrids come in three colors: yellow, white, and bicolor based on whether the parental lines are yellow or white. Cross-pollination of a yellow parental line by a white parental line will result in seed of a hybrid that when grown will produce bicolor ears Cross pollination of a yellow kernel hybrid by a bicolor or white kernel hybrid will not change the kernel color of the yellow hybrid, but may increase the percentage of yellow kernels on the bicolor or white kernel hybrids. This is due to the dominant nature of the allele for yellow kernel color. Although there are geographical preferences for certain kernel colors, there is no relationship between color and sweetness.

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possesses the traits to meet the program goals. The goal is to combine in a single variety or hybrid an improved combination of desirable traits from the parental germplasm.

In sweet corn these important traits include the ability of the seeds to emerge with vigor and uniformity, a strong plant type that resists lodging, a plant that carries some level of resistance for disease or insects, a high number of fresh ears or kernels that are produced on a unit of ground, good coverage of the husk leaves over the tip of the ear, easy removal of the ear from the stalk with a short shank attachment, a cylindrical ear shape and good balance between the ear's length and diameter, kernels arranged in 14 to 20 straight rows with good kernel depth and color, good kernel fill at the tip of the ear and good canned, frozen and/or fresh eating quality determined by the tenderness, aroma, sweetness and flavor of the sweet corn kernels.

In some embodiments, particularly desirable traits that may be incorporated by this invention are improved resistance to different viral, fungal, and bacterial pathogens. Important diseases include but are not limited to Northern Leaf blight (caused by *Exserohilum turcicum*, previously called *Helminthosporium turcicum*), Common Rust (caused by *Puccinia sorghi*), "Maize Dwarf Mosaic Virus (caused by MDMV strain A", Sugar Cane Mosaic Virus (caused by SCMV formally known as MDMV strain B), tropical rust (caused by the fungal pathogen *Physopella zeae* (Mains), grey leaf spot (fungal disease associated with *Cercospora* spp), Goss's wilt (caused by the bacterial pathogen *Clavibacter michiganensis* subsp. *nebraskensis* (CN)), Stewart's Bacterial Wilt (caused by *Paneoea stewartii*), High Plains Virus (caused by HPV)," etc. Improved resistance to insect pests is another desirable trait that may be incorporated into new sweet corn plants developed by this invention. Insect pests affecting the sweet corn include, but not limited to European corn borer, corn earworm, corn wireworm, Western bean cutworm fall armyworm, flea beetles, sap beetles etc.

Sweet Corn Breeding

The goal of sweet corn breeding is to develop new, unique and superior sweet corn inbred lines and hybrids. The breeder initially selects and crosses two or more parental lines, followed by repeated selfing and selection, producing many new genetic combinations. Another method used to develop new, unique and superior sweet corn inbred lines and hybrids occurs when the breeder selects and crosses two or more parental lines followed by haploid induction and chromosome doubling that result in the development of dihaploid inbred lines. The breeder can theoretically generate billions of different genetic combinations via crossing, selfing and mutations and the same is true for the utilization of the dihaploid breeding method.

During the development of new sweet corn inbreds and hybrids, the sweet corn breeder uses sweet corn plants, but also non sweet corn plants, as such non sweet corn plants may contain characteristics that the breeder has interest in having in its sweet corn inbreds and hybrids. Such non sweet corn plants could be regular field corn, or wild relatives of corn such as teosinte.

Each year, the plant breeder selects the germplasm to advance to the next generation. This germplasm is grown under unique and different geographical, climatic and soil conditions, and further selections are then made, during and at the end of the growing season. The inbred lines developed are unpredictable. This unpredictability is because the breeder's selection occurs in unique environments, with no control at the DNA level (using conventional breeding procedures or dihaploid breeding procedures), and with millions of different possible genetic combinations being generated. A breeder of ordinary skill in the art cannot predict the final resulting lines he develops, except possibly in a very broad and general fashion. This unpredictability results in the expenditure of large research monies to develop superior new sweet corn inbred lines and hybrids.

The development of commercial sweet corn hybrids requires the development of homozygous inbred lines, the crossing of these lines, and the evaluation of the hybrid crosses.

Pedigree breeding and recurrent selection breeding methods are used to develop inbred lines from breeding populations. Breeding programs combine desirable traits from two or more inbred lines or various broad-based sources into breeding pools from which inbred lines are developed by selfing and selection of desired phenotypes or through the dihaploid breeding method followed by the selection of desired phenotypes. The new inbreds are crossed with other inbred lines and the hybrids from these crosses are evaluated to determine which have commercial potential.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, recurrent selection, and backcross breeding.

i Pedigree Selection, Single and Multiple Seed Procedures

Pedigree breeding is used commonly for the improvement of self-pollinating crops or inbred lines of cross-pollinating crops. Two parents possessing favorable, complementary traits are crossed to produce an $F_1$. An $F_2$ population is produced by selfing one or several $F_1$s or by intercrossing two $F_1$s (sib mating). The dihaploid breeding method could also be used. Selection of the best individuals may begin in the $F_2$ population; with selection of the best individuals in the best families beginning in the F3 generation. In sweet corn early generation testing is generally not successful as an elite hybrid must carry many highly heritable traits together to be successful. Selection of these traits in combination acts more like a complex trait. It is important to be able to evaluate a uniform row or rows of a new hybrid to identify whether all the traits are present. In addition, replicated testing of the inbred families is not done until the elite hybrid combinations have been identified, as we look at many new F6 or dihaploid lines in combination each year, saving around 5% after hybrid evaluations.

Replicated testing of F5-F7 lines or dihaploid lines in hybrid combination is done using elite inbred lines as common testers. This begins the process of evaluating hybrids over several environments (locations and years) to determine which of these hybrids have the best chance for commercialization The single-seed descent procedure in the strict sense refers to planting a segregating population, harvesting a sample of one seed per plant, and using the one-seed sample to plant the next generation. When the population has been advanced from the F2 to the desired level of inbreeding, the plants from which lines are derived will each trace to different F2 individuals. The number of plants in a population declines each generation due to failure of some seeds to germinate or some plants to produce at least one seed. As a result, not all of the F2 plants originally sampled in the population will be represented by a progeny when generation advance is completed.

In a multiple-seed procedure, breeders commonly harvest one or more fruit containing seed from each plant in a population and blend them together to form a bulk seed lot. Part of the bulked seed is used to plant the next generation and part is put in reserve. The procedure has been referred to as modified single-seed descent or the bulk technique.

The multiple-seed procedure has been used to save labor at harvest. It is considerably faster than removing one seed from each fruit by hand for the single seed procedure. The multiple-seed procedure also makes it possible to plant the same number of seeds of a population each generation of inbreeding. Enough seeds are harvested to make up for those plants that did not germinate or produce seed.

Descriptions of other breeding methods that are commonly used for different traits and crops can be found in one of several reference books (e.g., R. W. Allard, 1960, Principles of Plant Breeding, John Wiley and Son, pp. 115-161; N. W. Simmonds, 1979, Principles of Crop Improvement, Longman Group Limited; W. R. Fehr, 1987, Principles of Crop Development, Macmillan Publishing Co.; N. F. Jensen, 1988, Plant Breeding Methodology, John Wiley & Sons).

ii Backcross Breeding

Backcross breeding has been used to transfer genes for a simply inherited, highly heritable trait into a desirable homozygous cultivar or inbred line which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the recurrent parent and the trait of interest from the donor parent are selected and repeatedly crossed (backcrossed) to the recurrent parent. The resulting plant is expected to have the attributes of the recurrent parent (e.g., cultivar) and the desirable trait transferred from the donor parent.

When the term sweet corn hybrid plant is used in the context of the present invention, this also includes any sweet corn hybrid plant where one or more desired trait has been introduced through backcrossing methods, whether such trait is a naturally occurring one, a mutant or a transgenic one. Backcrossing methods can be used with the present invention to improve or introduce one or more characteristic into the inbred parental line thus potentially introducing these traits in to the sweet corn hybrid plant of the present invention. The term "backcrossing" as used herein refers to the repeated crossing of a hybrid progeny back to the recurrent parent, i.e., backcrossing one, two, three, four, five, six, seven, eight, nine, or more times to the recurrent parent. The parental sweet corn plant which contributes the gene or the genes for the desired characteristic is termed the nonrecurrent or donor parent. This terminology refers to the fact that the nonrecurrent parent is used one time in the backcross protocol and therefore does not recur. The parental sweet corn plant to which the gene or genes from the nonrecurrent parent are transferred is known as the recurrent parent as it is used for several rounds in the backcrossing protocol.

In a typical backcross protocol, the original inbred of interest (recurrent parent) is crossed to a second inbred (nonrecurrent parent) that carries the gene or genes of interest to be transferred. The resulting progeny from this cross are then crossed again to the recurrent parent and the process is repeated until a sweet corn plant is obtained wherein all the desired morphological and physiological characteristics of the recurrent parent are recovered in the converted plant, generally determined at a 5% significance level when grown in the same environmental conditions, in addition to the gene or genes transferred from the nonrecurrent parent. It has to be noted that some, one, two, three or more, self-pollination and growing of population might be included between two successive backcrosses. Indeed, an appropriate selection in the population produced by the self-pollination, i.e. selection for the desired trait and physiological and morphological characteristics of the recurrent parent might be equivalent to one, two or even three additional backcrosses in a continuous series without rigorous selection, saving then time, money and effort to the breeder. A non-limiting example of such a protocol would be the following: a) the first generation F1 produced by the cross of the recurrent parent A by the donor parent B is backcrossed to parent A, b) selection is practiced for the plants having the desired trait of parent B, c) selected plant are self-pollinated to produce a population of plants where selection is practiced for the plants having the desired trait of parent B and physiological and morphological characteristics of parent A, d) the selected plants are backcrossed one, two, three, four, five, six, seven, eight, nine, or more times to parent A to produce selected backcross progeny plants comprising the desired trait of parent B and the physiological and morphological characteristics of parent A. Step (c) may or may not be repeated and included between the backcrosses of step (d).

The selection of a suitable recurrent parent is an important step for a successful backcrossing procedure. The goal of a backcross protocol is to alter or substitute one or more trait(s) or characteristic(s) in the original inbred parental line in order to find it then in the hybrid made thereof. To accomplish this, a gene or genes of the recurrent inbred is modified or substituted with the desired gene or genes from the nonrecurrent parent, while retaining essentially all of the rest of the desired genetic, and therefore the desired physiological and morphological constitution of the original inbred. The choice of the particular nonrecurrent parent will depend on the purpose of the backcross; one of the major purposes is to add some commercially desirable, agronomically important trait(s) to the plant. The exact backcrossing protocol will depend on the characteristic(s) or trait(s) being altered to determine an appropriate testing protocol. Although backcrossing methods are simplified when the characteristic being transferred is a single gene and dominant allele, multiple genes and recessive allele(s) may also be transferred and therefore, backcross breeding is by no means restricted to character(s) governed by one or a few genes. In fact the number of genes might be less important that the identification of the character(s) in the segregating population. In this instance it may then be necessary to introduce a test of the progeny to determine if the desired characteristic(s) has been successfully transferred. Such tests encompass visual inspection, simple crossing, but also follow up of the characteristic(s) through genetically associated markers and molecular assisted breeding tools. For example, selection of progeny containing the transferred trait is done by direct selection, visual inspection for a trait associated with a dominant allele, while the selection of progeny for a trait that is transferred via a recessive allele, such as the shrunken-2 starch mutant in corn, require selfing the progeny or using molecular markers to determine which plant carry the recessive allele(s).

In 1981, the backcross method of breeding counted for 17% of the total breeding effort for inbred line development in the United States, accordingly to, Hallauer, A. R. et al. (1988) "Corn Breeding" Corn and Corn Improvement, No. 18, pp. 463-481.

The backcross breeding method provides a precise way of improving varieties that excel in a large number of attributes but are deficient in a few characteristics. (Page 150 of the Pr. R. W. Allard's 1960 book, published by John Wiley & Sons, Inc, *Principles of Plant Breeding*). The method makes use of a series of backcrosses to the variety to be improved during which the character or the characters in which improvement is sought is maintained by selection. At the end of the backcrossing the gene or genes being transferred unlike all other genes, will be heterozygous. Selfing after the last backcross produces homozygosity for this gene pair(s) and, coupled with selection, will result in a parental line of a hybrid variety with exactly or essentially the same adaptation, yielding ability and quality characteristics of the recurrent parent but superior to that parent in the particular characteristic(s) for which the improvement program was undertaken. Therefore, this method provides the plant breeder with a high degree of genetic control of his work.

The method is scientifically exact because the morphological and agricultural features of the improved variety could be described in advance and because a similar variety could, if it were desired, be bred a second time by retracing the same steps (Briggs, "Breeding wheats resistant to bunt by the backcross method", 1930 *Jour. Amer. Soc. Agron.,* 22: 289-244).

Backcrossing is a powerful mechanism for achieving homozygosity and any population obtained by backcrossing must rapidly converge on the genotype of the recurrent parent. When backcrossing is made the basis of a plant breeding program, the genotype of the recurrent parent will be theoretically modified only with regards to genes being transferred, which are maintained in the population by selection.

Successful backcrosses are, for example, the transfer of stem rust resistance from 'Hope' wheat to 'Bart wheat' and even pursuing the backcrosses with the transfer of bunt resistance to create 'Bart 38', having both resistances. Also highlighted by Allard is the successful transfer of mildew, leaf spot and wilt resistances in California Common alfalfa to create 'Caliverde'. This new 'Caliverde' variety produced through the backcross process is indistinguishable from California Common except for its resistance to the three named diseases.

One of the advantages of the backcross method is that the breeding program can be carried out in almost every environment that will allow the development of the character being transferred or when using molecular markers that can identify the trait of interest.

The backcross technique is not only desirable when breeding for disease resistance but also for the adjustment of morphological characters, colour characteristics and simply inherited quantitative characters such as earliness, plant height and seed size and shape. In this regard, a medium grain type variety, 'Calady', has been produced by Jones and Davis. As dealing with quantitative characteristics, they selected the donor parent with the view of sacrificing some of the intensity of the character for which it was chosen, i.e. grain size. 'Lady Wright', a long grain variety was used as the donor parent and 'Coloro', a short grain one as the recurrent parent. After four backcrosses, the medium grain type variety 'Calady' was produced.

iii Open-Pollinated Populations

The improvement of open-pollinated populations of such crops as rye, many maizes and sugar beets, herbage grasses, legumes such as alfalfa and clover, and tropical tree crops such as cacao, coconuts, oil palm and some rubber, depends essentially upon changing gene-frequencies towards fixation of favorable alleles while maintaining a high (but far from maximal) degree of heterozygosity.

Uniformity in such populations is impossible and trueness-to-type in an open-pollinated variety is a statistical feature of the population as a whole, not a characteristic of individual plants. Thus, the heterogeneity of open-pollinated populations contrasts with the homogeneity (or virtually so) of inbred lines, clones and hybrids.

Population improvement methods fall naturally into two groups, those based on purely phenotypic selection, normally called mass selection, and those based on selection with progeny testing. Interpopulation improvement utilizes the concept of open breeding populations; allowing genes to flow from one population to another. Plants in one population (cultivar, strain, ecotype, or any germplasm source) are crossed either naturally (e.g., by wind) or by hand or by bees (commonly *Apis mellifera* L. or *Megachile rotundata* F.) with plants from other populations. Selection is applied to improve one (or sometimes both) population(s) by isolating plants with desirable traits from both sources.

There are basically two primary methods of open-pollinated population improvement.

First, there is the situation in which a population is changed en masse by a chosen selection procedure. The outcome is an improved population that is indefinitely propagated by random-mating within itself in isolation.

Second, the synthetic variety attains the same end result as population improvement, but is not itself propagated as such; it has to be reconstructed from parental lines or clones. These plant breeding procedures for improving open-pollinated populations are well known to those skilled in the art and comprehensive reviews of breeding procedures routinely used for improving cross-pollinated plants are provided in numerous texts and articles, including: Allard, *Principles of Plant Breeding*, John Wiley & Sons, Inc. (1960); Simmonds, *Principles of Crop Improvement*, Longman Group Limited (1979); Hallauer and Miranda, *Quantitative Genetics in Maize Breeding*, Iowa State University Press (1981); and, Jensen, *Plant Breeding Methodology*, John Wiley & Sons, Inc. (1988).

A) Mass Selection

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued. In mass selection, desirable individual plants are chosen, harvested, and the seed composited without progeny testing to produce the following generation. Since selection is based on the maternal parent only, and there is no control over pollination, mass selection amounts to a form of random mating with selection. As stated above, the purpose of mass selection is to increase the proportion of superior genotypes in the population.

B) Synthetics

A synthetic variety is produced by intercrossing a number of genotypes selected for good combining ability in all possible hybrid combinations, with subsequent maintenance of the variety by open pollination. Whether parents are (more or less inbred) seed-propagated lines, as in some sugar beet and beans (*Vicia*) or clones, as in herbage grasses, clovers and alfalfa, makes no difference in principle. Parents are selected on general combining ability, sometimes by test crosses or toperosses, more generally by polycrosses. Parental seed lines may be deliberately inbred (e.g. by selfing or sib crossing). However, even if the parents are not deliberately inbred, selection within lines during line maintenance will ensure that some inbreeding occurs. Clonal parents will, of course, remain unchanged and highly heterozygous.

Whether a synthetic can go straight from the parental seed production plot to the farmer or must first undergo one or more cycles of multiplication depends on seed production and the scale of demand for seed. In practice, grasses and clovers are generally multiplied once or twice and are thus considerably removed from the original synthetic.

While mass selection is sometimes used, progeny testing is generally preferred for polycrosses, because of their operational simplicity and obvious relevance to the objective, namely exploitation of general combining ability in a synthetic.

The number of parental lines or clones that enters a synthetic varies widely. In practice, numbers of parental lines range from 10 to several hundred, with 100-200 being the average. Broad based synthetics formed from 100 or more clones would be expected to be more stable during seed multiplication than narrow based synthetics.

iv. Hybrids

A hybrid is an individual plant resulting from a cross between parents of differing genotypes. Commercial hybrids are now used extensively in many crops, including corn (maize), sorghum, sugarbeet, sunflower and broccoli. Hybrids can be formed in a number of different ways, including by crossing two parents directly (single cross hybrids), by crossing a single cross hybrid with another parent (three-way or triple cross hybrids), or by crossing two different hybrids (four-way or double cross hybrids).

Strictly speaking, most individuals in an out breeding (i.e., open-pollinated) population are hybrids, but the term is usually reserved for cases in which the parents are individuals whose genomes are sufficiently distinct for them to be recognized as different species or subspecies. Hybrids may be fertile or sterile depending on qualitative and/or quantitative differences in the genomes of the two parents. Heterosis, or hybrid vigor, is usually associated with increased heterozygosity that results in increased vigor of growth, survival, and fertility of hybrids as compared with the parental lines that were used to form the hybrid. Maximum heterosis is usually achieved by crossing two genetically different, highly inbred lines.

Hybrid sweet corn seed is typically produced by removing the tassels from the female parent or by using a male sterile female incorporating manual or mechanical detasseling. Alternate strips of two sweet corn inbreds are planted in a field, and the pollen-bearing tassels are removed from one of the inbreds (female). Providing that there is sufficient isolation from sources of foreign corn pollen, the ears of the detasseled inbred will be fertilized only from the other inbred (male), and the resulting seed is therefore hybrid and will form hybrid plants.

The laborious, and occasionally unreliable, detasseling process can be avoided by using cytoplasmic male-sterile (CMS) inbreds. Plants of a CMS inbred are male sterile as a result of factors resulting from the cytoplasmic, as opposed to the nuclear, genome. Thus, this characteristic is inherited exclusively through the female parent in corn plants, since only the female provides cytoplasm to the fertilized seed. CMS plants are fertilized with pollen from another inbred that is not male-sterile. Pollen from the second inbred may or may not contribute genes that make the hybrid plants male-fertile. Seed from detasseled fertile corn and CMS produced seed of the same hybrid can be blended to insure that adequate pollen loads are available for fertilization when the hybrid plants are grown.

There are several methods of conferring genetic male sterility available, such as multiple mutant genes at separate locations within the genome that confer male sterility, as disclosed in U.S. Pat. Nos. 4,654,465 and 4,727,219 to Brar et al. and chromosomal translocations as described by Patterson in U.S. Pat. Nos. 3,861,709 and 3,710,511. These and all patents referred to are incorporated by reference. In addition to these methods, Albertsen et al., U.S. Pat. No. 5,432,068 have developed a system of nuclear male sterility which includes: identifying a gene which is critical to male fertility, silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on", the promoter, which in turn allows the gene that confers male fertility to be transcribed.

There are many other methods of conferring genetic male sterility in the art, each with its own benefits and drawbacks. These methods use a variety of approaches such as delivering into the plant a gene encoding a cytotoxic substance associated with a male tissue specific promoter or an antisense system in which a gene critical to fertility is identified and an antisense to that gene is inserted in the plant (see, Fabinjanski, et al. EPO 89/3010153.8 publication no. 329, 308 and PCT application PCT/CA90/00037 published as WO 90/08828).

Another version useful in controlling male sterility makes use of gametocides. Gametocides are not a genetic system, but rather a topical application of chemicals. These chemicals affect cells that are critical to male fertility. The application of these chemicals affects fertility in the plants only for the growing season in which the gametocide is applied (see Carlson, G. R., U.S. Pat. No. 4,936,904). Application of the gametocide, timing of the application and genotype specifically often limit the usefulness of the approach.

Once the inbreds that give the best hybrid performance have been identified, the hybrid seed can be reproduced indefinitely as long as the homogeneity of the inbred parent is maintained. A single-cross hybrid is produced when two inbred lines are crossed to produce the F1 progeny. A double-cross hybrid is produced from four inbred lines crossed in pairs (A×B and C×D) and then the two F1 hybrids are crossed again (A×B)×(C×D). Much of the hybrid vigor and uniformity exhibited by F1 hybrids is lost in the next generation (F2). Consequently, seed from F2 hybrid varieties is not used for planting stock.

The production of hybrids is a well-developed industry, involving the isolated production of both the parental lines and the hybrids which result from crossing those lines. For a detailed discussion of the hybrid production process, see, e.g., Wright, *Commercial Hybrid Seed Production* 8:161-176, In Hybridization of Crop Plants.

v. Bulk Segregation Analysis (BSA)

BSA, a.k.a. bulked segregation analysis, or bulk segregant analysis, is a method described by Michelmore et al. (Michelmore et al., 1991, Identification of markers linked to disease-resistance genes by bulked segregant analysis: a rapid method to detect markers in specific genomic regions by using segregating populations. *Proceedings of the National Academy of Sciences*, USA, 99:9828-9832) and Quarrie et al. (Quarrie et al., 1999, *Journal of Experimental Botany*, 50(337): 1299-1306).

For BSA of a trait of interest, parental lines with certain different phenotypes are chosen and crossed to generate F2, doubled haploid or recombinant inbred populations with QTL analysis. The population is then phenotyped to identify individual plants or lines having high or low expression of the trait. Two DNA bulks are prepared, one from the individuals having one phenotype (e.g., resistant to virus), and the other from the individuals having reversed phenotype (e.g., susceptible to virus), and analyzed for allele frequency with molecular markers. Only a few individuals are required in each bulk (e.g., 10 plants each) if the markers are dominant (e.g., RAPDs). More individuals are needed when markers are co-dominant (e.g., RFLPs, SNPs or SSRs). Markers linked to the phenotype can be identified and used for breeding or QTL mapping.

vi. Hand-Pollination Method

Hand pollination describes the crossing of plants via the deliberate fertilization of female ovules with pollen from a desired male parent plant. In some embodiments the donor or recipient female parent and the donor or recipient male parent line are planted in the same field. The inbred male parent can be planted earlier or later than the female parent to ensure adequate pollen supply at the pollination time. In some embodiments, the male parent and female parent can be planted at a ratio of 1 male parent to 2-6 female parents. The male parent may be planted at the top of the field for efficient male pollen collection during pollination. Pollination is started when the female parent flower is ready to be fertilized and there is available pollen from the male parent. Female ear shoots that are ready to open in the following days are identified, covered with paper cups or small paper bags that prevent bee or any other insect from visiting the female flowers, and marked with any kind of material that can be easily seen the next morning. The male pollen of the male parent is collected after it is likely that there is new pollen available from that days shedding. The covered female flowers of the female parent, which have ear silk showing, are un-covered and pollinated with the collected fresh male pollen of the male parent, starting as soon as the male flower sheds pollen. The pollinated female flowers are again covered after pollination to contamination by other pollen traveling by wind or by bees and any other insects. The pollinated female flowers are also marked. The marked fruits or ears are harvested. In some embodiments, the male pollen used for fertilization has been previously collected and stored.

vii. Targeting Induced Local Lesions in Genomes (TILL-ING)

Breeding schemes of the present application can include crosses with TILLING® plant lines. TILLING® is a method in molecular biology that allows directed identification of mutations in a specific gene. TILLING® was introduced in 2000, using the model plant *Arabidopsis thaliana*. TILLING® has since been used as a reverse genetics method in other organisms such as zebrafish, corn, wheat, rice, soybean, tomato and lettuce.

The method combines a standard and efficient technique of mutagenesis with a chemical mutagen (e.g., Ethyl methanesulfonate (EMS)) with a sensitive DNA screening-technique that identifies single base mutations (also called point mutations) in a target gene. EcoTILLING is a method that uses TILLING® techniques to look for natural mutations in individuals, usually for population genetics analysis (see Comai, et al., 2003 The Plant Journal 37, 778-786; Gilchrist et al. 2006 Mol. Ecol. 15, 1367-1378; Mejlhede et al. 2006 Plant Breeding 125, 461-467; Nieto et al. 2007 BMC Plant Biology 7, 34-42, each of which is incorporated by reference hereby for all purposes). DEcoTILLING is a modification of TILLING® and EcoTILLING which uses an inexpensive method to identify fragments (Garvin et al., 2007, DEcoTILLING: An inexpensive method for SNP discovery that reduces ascertainment bias. Molecular Ecology Notes 7, 735-746).

The TILLING® method relies on the formation of heteroduplexes that are formed when multiple alleles (which could be from a heterozygote or a pool of multiple homozygotes and heterozygotes) are amplified in a PCR, heated, and then slowly cooled. As DNA bases are not pairing at the mismatch of the two DNA strands (the induced mutation in TILLING® or the natural mutation or SNP in EcoTILLING), they provoke a shape change in the double strand DNA fragment which is then cleaved by single stranded nucleases. The products are then separated by size on several different platforms.

Several TILLING® centers exists over the world that focus on agriculturally important species: UC Davis (USA), focusing on Rice; Purdue University (USA), focusing on Maize; University of British Columbia (CA), focusing on *Brassica napus*; John Innes Centre (UK), focusing on *Brassica rapa*; Fred Hutchinson Cancer Research, focusing on *Arabidopsis*; Southern Illinois University (USA), focusing on Soybean; John Innes Centre (UK), focusing on Lotus and Medicago; and INRA (France), focusing on Pea and Tomato.

More detailed description on methods and compositions on TILLING® can be found in U.S. Pat. No. 5,994,075, US 2004/0053236 A1, WO 2005/055704, and WO 2005/048692, each of which is hereby incorporated by reference for all purposes.

Thus in some embodiments, the breeding methods of the present disclosure include breeding with one or more TILLING plant lines with one or more identified mutations.

viii Mutation Breeding

Mutation breeding is another method of introducing new variation and subsequent traits into sweet corn plants. Mutations that occur spontaneously or are artificially induced can be useful sources of variability for a plant breeder. The goal of artificial mutagenesis is to increase the rate of mutation for a desired characteristic. Mutation rates can be increased by many different means or mutating agents including temperature, long-term seed storage, tissue culture conditions, radiation (such as X-rays, Gamma rays, neutrons, Beta radiation, or ultraviolet radiation), chemical mutagens (such as base analogs like 5-bromo-uracil), antibiotics, alkylating agents (such as sulfur mustards, nitrogen mustards, epoxides, ethyleneamines, sulfates, sulfonates, sulfones, or lactones), azide, hydroxylamine, nitrous acid or acridines. Once a desired trait is observed through mutagenesis the trait may then be incorporated into existing germplasm by traditional breeding techniques. Details of mutation breeding can be found in W. R. Fehr, 1993, Principles of Cultivar Development, Macmillan Publishing Co.

New breeding techniques such as the ones involving the uses of Zinc Finger Nucleases or oligonucleotide directed mutagenesis shall also be used to generate genetic variability and introduce new traits into sweet corn varieties.

ix. Double Haploids and Chromosome Doubling

One way to obtain homozygous plants without the need to cross two parental lines followed by a long selection of the segregating progeny, and/or multiple backcrossings is to produce haploids and then double the chromosomes to form doubled haploids. Haploid plants can occur spontaneously, or may be artificially induced via chemical treatments or by crossing plants with inducer lines (Seymour et al. 2012, PNAS vol 109, pg 4227-4232; Zhang et al., 2008 Plant Cell Rep. December 27(12) 1851-60). The production of haploid progeny can occur via a variety of mechanisms which can affect the distribution of chromosomes during gamete formation. The chromosome complements of haploids sometimes double spontaneously to produce homozygous doubled haploids (DHs). Mixoploids, which are plants which contain cells having different ploidies, can sometimes arise and may represent plants that are undergoing chromosome doubling so as to spontaneously produce doubled haploid tissues, organs, shoots, floral parts or plants. Another common technique is to induce the formation of double haploid plants with a chromosome doubling treatment such as colchicine (El-Hennawy et al., 2011 Vol 56, issue 2 pg 63-72; Doubled Haploid Production in Crop Plants 2003 edited by Maluszynski ISBN 1-4020-1544-5). The production of doubled haploid plants yields highly uniform inbred lines and is especially desirable as an alternative to sexual inbreeding of longer-generation crops. By producing doubled haploid progeny, the number of possible gene combinations for inherited traits is more manageable. Thus, an efficient doubled haploid technology can significantly reduce the time and the cost of inbred and cultivar development.

x. Protoplast Fusion

In another method for breeding plants, protoplast fusion can also be used for the transfer of trait-conferring genomic material from a donor plant to a recipient plant. Protoplast fusion is an induced or spontaneous union, such as a somatic hybridization, between two or more protoplasts (cells of which the cell walls are removed by enzymatic treatment) to produce a single bi- or multi-nucleate cell. The fused cell that may even be obtained with plant species that cannot be interbred in nature is tissue cultured into a hybrid plant exhibiting the desirable combination of traits.

xi. Embryo Rescue

Alternatively, embryo rescue may be employed in the transfer of resistance-conferring genomic material from a donor plant to a recipient plant. Embryo rescue can be used as a procedure to isolate embryo's from crosses to rapidly move to the next generation of backcrossing or selfing or wherein plants fail to produce viable seed. In this process, the fertilized ovary or immature seed of a plant is tissue cultured to create new plants (see Pierik, 1999, In vitro culture of higher plants, Springer, ISBN 079235267x, 9780792352679, which is incorporated herein by reference in its entirety).

Breeding Evaluation

Each breeding program can include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested per se and in hybrid combination and compared to appropriate standards in environments representative of the commercial target area(s). The best lines are candidates for use as parents in new commercial cultivars; those still deficient in a few traits may be used as parents to produce new populations for further selection or in a backcross program to improve the parent lines for a specific trait.

In one embodiment, the plants are selected on the basis of one or more phenotypic traits. Skilled persons will readily appreciate that such traits include any observable characteristic of the plant, including for example growth rate, vigor, plant health, maturity, tillering, standability or tolerance to lodging, plant height, stalk weight, leaf area or orientation, height, weight, color, taste, smell, changes in the production of one or more compounds by the plant (including for example, metabolites, proteins, drugs, carbohydrates, oils, and any other compounds).

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer; for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

It should be appreciated that in certain embodiments, plants may be selected based on the absence, suppression or inhibition of a certain feature or trait (such as an undesirable feature or trait) as opposed to the presence of a certain feature or trait (such as a desirable feature or trait).

Selecting plants based on genotypic information is also envisaged (for example, including the pattern of plant gene expression, genotype, or presence of genetic markers). Where the presence of one or more genetic marker is assessed, the one or more marker may already be known and/or associated with a particular characteristic of a plant; for example, a marker or markers may be associated with an increased growth rate or metabolite profile. This information could be used in combination with assessment based on other characteristics in a method of the disclosure to select for a combination of different plant characteristics that may be desirable. Such techniques may be used to identify novel quantitative trait loci (QTLs). By way of example, plants may be selected based on growth rate, size (including but not limited to weight, height, leaf size, stem size, branching pattern, or the size of any part of the plant), general health, survival, tolerance to adverse physical environments and/or any other characteristic, as described herein before.

Further non-limiting examples include selecting plants based on: speed of seed germination; quantity of biomass produced; increased root, and/or leaf/shoot growth that leads to an increased yield (herbage or grain or fiber or oil) or biomass production; effects on plant growth that results in an increased seed yield for a crop; effects on plant growth which result in an increased yield; effects on plant growth that lead to an increased resistance or tolerance to disease including fungal, viral or bacterial diseases, to *mycoplasma* or to pests such as insects, mites or nematodes in which damage is measured by decreased foliar symptoms such as the incidence of bacterial or fungal lesions, or area of damaged foliage or reduction in the numbers of nematode cysts or galls on plant roots, or improvements in plant yield in the presence of such plant pests and diseases; effects on plant growth that lead to increased metabolite yields; effects on plant growth that lead to improved aesthetic appeal which may be particularly important in plants grown for their form, color or taste, for example the color or the taste of the kernels.

Molecular Breeding Evaluation Techniques

Selection of plants based on phenotypic or genotypic information may be performed using techniques such as, but not limited to: high through-put screening of chemical components of plant origin, sequencing techniques including high through-put sequencing of genetic material, differential display techniques (including DDRT-PCR, and DD-PCR), nucleic acid microarray techniques, RNA-seq (transcriptome sequencing), qRTPCR (quantitative real time PCR).

In one embodiment, the evaluating step of a plant breeding program involves the identification of desirable traits in progeny plants. Progeny plants can be grown in, or exposed to conditions designed to emphasize a particular trait (e.g. drought conditions for drought tolerance, lower temperatures for freezing tolerant traits). Progeny plants with the highest scores for a particular trait may be used for subsequent breeding steps.

In some embodiments, plants selected from the evaluation step can exhibit a 1%, 5%, 10%, 15%, 20%, 25%, 30%, 35%, 40%, 45%, 50%, 55%, 60%, 65%, 70%, 75%, 80%, 85%, 90%, 95%, 100%, 120% or more improvement in a particular plant trait compared to a control plant.

In other embodiments, the evaluating step of plant breeding comprises one or more molecular biological tests for genes or other markers. For example, the molecular biological test can involve probe hybridization and/or amplification of nucleic acid (e.g., measuring nucleic acid density by Northern or Southern hybridization, PCR) and/or immunological detection (e.g., measuring protein density, such as precipitation and agglutination tests, ELISA (e.g., Lateral Flow test or DAS-ELISA), Western blot, immune labeling, immunosorbent electron microscopy (ISEM), and/or dot blot).

The procedure to perform a nucleic acid hybridization, an amplification of nucleic acid (e.g., PCR, RT-PCR) or an immunological detection (e.g., precipitation and agglutination tests, ELISA (e.g., Lateral Flow test or DAS-ELISA), Western blot, RIA, immunogold or immunofluorescent labeling, immunosorbent electron microscopy (ISEM), and/or dot blot tests) are performed as described elsewhere herein and well-known by one skilled in the art.

In one embodiment, the evaluating step comprises PCR (semi-quantitative or quantitative), wherein primers are used to amplify one or more nucleic acid sequences of a desirable gene, or a nucleic acid associated with said gene or QTL or a desirable trait (e.g., a co-segregating nucleic acid, or other marker).

In another embodiment, the evaluating step comprises immunological detection (e.g., precipitation and agglutination tests, ELISA (e.g., Lateral Flow test or DAS-ELISA), Western blot, RIA, immuno labeling (gold, fluorescent, or other detectable marker), immunosorbent electron microscopy (ISEM), and/or dot blot), wherein one or more gene or marker-specific antibodies are used to detect one or more desirable proteins. In one embodiment, said specific antibody is selected from the group consisting of polyclonal antibodies, monoclonal antibodies, antibody fragments, and combination thereof.

Reverse Transcription Polymerase Chain Reaction (RT-PCR) can be utilized in the present disclosure to determine expression of a gene to assist during the selection step of a breeding scheme. It is a variant of polymerase chain reaction (PCR), a laboratory technique commonly used in molecular biology to generate many copies of a DNA sequence, a process termed "amplification". In RT-PCR, however, RNA strand is first reverse transcribed into its DNA complement (complementary DNA, or cDNA) using the enzyme reverse transcriptase, and the resulting cDNA is amplified using traditional or real-time PCR.

RT-PCR utilizes a pair of primers, which are complementary to a defined sequence on each of the two strands of the mRNA. These primers are then extended by a DNA polymerase and a copy of the strand is made after each cycle, leading to logarithmic amplification.

RT-PCR includes three major steps. The first step is the reverse transcription (RT) where RNA is reverse transcribed to cDNA using a reverse transcriptase and primers. This step is very important in order to allow the performance of PCR since DNA polymerase can act only on DNA templates. The RT step can be performed either in the same tube with PCR (one-step PCR) or in a separate one (two-step PCR) using a temperature between 40° C. and 50° C., depending on the properties of the reverse transcriptase used.

The next step involves the denaturation of the dsDNA at 95° C., so that the two strands separate and the primers can bind again at lower temperatures and begin a new chain reaction. Then, the temperature is decreased until it reaches the annealing temperature which can vary depending on the set of primers used, their concentration, the probe and its concentration (if used), and the cation concentration. The main consideration, of course, when choosing the optimal annealing temperature is the melting temperature (Tm) of the primers and probes (if used). The annealing temperature chosen for a PCR depends directly on length and composition of the primers. This is the result of the difference of hydrogen bonds between A-T (2 bonds) and G-C (3 bonds). An annealing temperature about 5 degrees below the lowest Tm of the pair of primers is usually used.

The final step of PCR amplification is the DNA extension from the primers which is done by the thermostable Taq DNA polymerase usually at 72° C., which is the optimal temperature for the polymerase to work. The length of the incubation at each temperature, the temperature alterations and the number of cycles are controlled by a programmable thermal cycler. The analysis of the PCR products depends on the type of PCR applied. If a conventional PCR is used, the PCR product is detected using for example agarose gel electrophoresis or other polymer gel like polyacrylamide gels and ethidium bromide (or other nucleic acid staining).

Conventional RT-PCR is a time-consuming technique with important limitations when compared to real time PCR techniques. Furthermore, the specificity of the assay is mainly determined by the primers, which can give false-positive results. However, the most important issue concerning conventional RT-PCR is the fact that it is a semi or even a low quantitative technique, where the amplicon can be visualized only after the amplification ends.

Real time RT-PCR provides a method where the amplicons can be visualized as the amplification progresses using a fluorescent reporter molecule. There are three major kinds of fluorescent reporters used in real time RT-PCR, general non specific DNA Binding Dyes such as SYBR Green I, TaqMan Probes and Molecular Beacons (including Scorpions).

The real time PCR thermal cycler has a fluorescence detection threshold, below which it cannot discriminate the difference between amplification generated signal and background noise. On the other hand, the fluorescence increases as the amplification progresses and the instrument performs data acquisition during the annealing step of each cycle. The number of amplicons will reach the detection baseline after a specific cycle, which depends on the initial concentration of the target DNA sequence. The cycle at which the instrument can discriminate the amplification generated fluorescence from the background noise is called the threshold cycle (Ct). The higher is the initial DNA concentration, the lower its Ct will be.

Other forms of nucleic acid detection can include next generation sequencing methods such as DNA SEQ or RNA SEQ using any known sequencing platform including, but not limited to: Roche 454, Solexa Genome Analyzer, AB SOLiD, Illumina GA/HiSeq, Ion PGM, Mi Seq, among others (Liu et al., 2012 Journal of Biomedicine and Biotechnology Volume 2012 ID 251364; Franca et al., 2002 Quarterly Reviews of Biophysics 35 pg 169-200; Mardis 2008 Genomics and Human Genetics vol 9 pg 387-402).

In other embodiments, nucleic acids may be detected with other high throughput hybridization technologies including microarrays, gene chips, LNA probes, nanoStrings, and fluorescence polarization detection among others.

In some embodiments, detection of markers can be achieved at an early stage of plant growth by harvesting a small tissue sample (e.g., branch, or leaf disk). This approach is preferable when working with large populations as it allows breeders to weed out undesirable progeny at an early stage and conserve growth space and resources for progeny which show more promise. In some embodiments the detection of markers is automated, such that the detection and storage of marker data is handled by a machine. Recent advances in robotics have also led to full service analysis tools capable of handling nucleic acid/protein marker extractions, detection, storage and analysis.

Quantitative Trait Loci

Breeding schemes of the present application can include crosses between donor and recipient plants. In some embodiments said donor plants contain a gene or genes of interest which may confer the plant with a desirable phenotype. The recipient line can be an elite line having certain favorite traits such for commercial production. In one embodiment, the elite line may contain other genes that also impart said line with the desired phenotype. When crossed together, the donor and recipient plant may create a progeny plant with combined desirable loci which may provide quantitatively additive effect of a particular characteristic. In that case, QTL mapping can be involved to facilitate the breeding process.

A QTL (quantitative trait locus) mapping can be applied to determine the parts of the donor plant's genome conferring the desirable phenotype, and facilitate the breeding methods. Inheritance of quantitative traits or polygenic inheritance refers to the inheritance of a phenotypic characteristic that varies in degree and can be attributed to the interactions between two or more genes and their environment. Though not necessarily genes themselves, quantitative trait loci (QTLs) are stretches of DNA that are closely linked to the genes that underlie the trait in question. QTLs can be molecularly identified to help map regions of the genome that contain genes involved in specifying a quantitative trait. This can be an early step in identifying and sequencing these genes.

Typically, QTLs underlie continuous traits (those traits that vary continuously, e.g. yield, height, level of resistance to virus, etc.) as opposed to discrete traits (traits that have two or several character values, e.g. smooth vs. wrinkled peas used by Mendel in his experiments). Moreover, a single phenotypic trait is usually determined by many genes. Consequently, many QTLs are associated with a single trait.

A quantitative trait locus (QTL) is a region of DNA that is associated with a particular phenotypic trait. Knowing the number of QTLs that explains variation in the phenotypic trait tells about the genetic architecture of a trait. It may tell that a trait is controlled by many genes of small effect, or by a few genes of large effect or by a several genes of small effect and few genes of larger effect.

Another use of QTLs is to identify candidate genes underlying a trait. Once a region of DNA is identified as contributing to a phenotype, it can be sequenced. The DNA sequence of any genes in this region can then be compared to a database of DNA for genes whose function is already known.

In a recent development, classical QTL analyses are combined with gene expression profiling i.e. by DNA microarrays. Such expression QTLs (e-QTLs) describes cis- and trans-controlling elements for the expression of often disease-associated genes. Observed epistatic effects have been found beneficial to identify the gene responsible by a cross-validation of genes within the interacting loci with metabolic pathway- and scientific literature databases.

QTL mapping is the statistical study of the alleles that occur in a locus and the phenotypes (physical forms or traits) that they produce (see, Meksem and Kahl, *The handbook of plant genome mapping: genetic and physical mapping*, 2005, Wiley-VCH, ISBN 3527311165, 9783527311163). Because most traits of interest are governed by more than one gene, defining and studying the entire locus of genes related to a trait gives hope of understanding what effect the genotype of an individual might have in the real world.

Statistical analysis is required to demonstrate that different genes interact with one another and to determine whether they produce a significant effect on the phenotype. QTLs identify a particular region of the genome as containing one or several genes, i.e. a cluster of genes that is associated with the trait being assayed or measured. They are shown as intervals across a chromosome, where the probability of association is plotted for each marker used in the mapping experiment.

To begin, a set of genetic markers must be developed for the species in question. A marker is an identifiable region of variable DNA. Biologists are interested in understanding the genetic basis of phenotypes (physical traits). The aim is to find a marker that is significantly more likely to co-occur with the trait than expected by chance, that is, a marker that has a statistical association with the trait. Ideally, they would be able to find the specific gene or genes in question, but this is a long and difficult undertaking. Instead, they can more readily find regions of DNA that are very close to the genes in question. When a QTL is found, it is often not the actual gene underlying the phenotypic trait, but rather a region of DNA that is closely linked with the gene.

For organisms whose genomes are known, one might now try to exclude genes in the identified region whose function is known with some certainty not to be connected with the trait in question. If the genome is not available, it may be an option to sequence the identified region and determine the putative functions of genes by their similarity to genes with known function, usually in other genomes. This can be done using BLAST, an online tool that allows users to enter a primary sequence and search for similar sequences within the BLAST database of genes from various organisms.

Another interest of statistical geneticists using QTL mapping is to determine the complexity of the genetic architecture underlying a phenotypic trait. For example, they may be interested in knowing whether a phenotype is shaped by many independent loci, or by a few loci, and how do those loci interact. This can provide information on how the phenotype may be evolving.

Molecular markers are used for the visualization of differences in nucleic acid sequences. This visualization is possible due to DNA-DNA hybridization techniques (RFLP) and/or due to techniques using the polymerase chain reaction (e.g. STS, SNPs, microsatellites, AFLP). All differences between two parental genotypes will segregate in a mapping population based on the cross of these parental genotypes. The segregation of the different markers may be compared and recombination frequencies can be calculated. The recombination frequencies of molecular markers on different chromosomes are generally 50%. Between molecular markers located on the same chromosome the recombination frequency depends on the distance between the markers. A low recombination frequency usually corresponds to a low distance between markers on a chromosome. Comparing all recombination frequencies will result in the most logical order of the molecular markers on the chromosomes. This most logical order can be depicted in a linkage map (Paterson, 1996, Genome Mapping in Plants. R. G. Landes, Austin.). A group of adjacent or contiguous markers on the linkage map that is associated to a reduced disease incidence and/or a reduced lesion growth rate pinpoints the position of a QTL.

The nucleic acid sequence of a QTL may be determined by methods known to the skilled person. For instance, a nucleic acid sequence comprising said QTL or a resistance-conferring part thereof may be isolated from a donor plant by fragmenting the genome of said plant and selecting those fragments harboring one or more markers indicative of said QTL. Subsequently, or alternatively, the marker sequences (or parts thereof) indicative of said QTL may be used as (PCR) amplification primers, in order to amplify a nucleic acid sequence comprising said QTL from a genomic nucleic acid sample or a genome fragment obtained from said plant. The amplified sequence may then be purified in order to obtain the isolated QTL. The nucleotide sequence of the QTL, and/or of any additional markers comprised therein, may then be obtained by standard sequencing methods.

One or more such QTLs associated with a desirable trait in a donor plant can be transferred to a recipient plant to incorporate the desirable trait into progeny plants by transferring and/or breeding methods.

In one embodiment, an advanced backcross QTL analysis (AB-QTL) is used to discover the nucleotide sequence or the QTLs responsible for the resistance of a plant. Such method was proposed by Tanksley and Nelson in 1996 (Tanksley and Nelson, 1996, Advanced backcross QTL analysis: a method for simultaneous discovery and transfer of valuable QTL from un-adapted germplasm into elite breeding lines. *Theor Appl Genet* 92:191-203) as a new breeding method that integrates the process of QTL discovery with variety development, by simultaneously identifying and transferring useful QTL alleles from un-adapted (e.g., land races, wild species) to elite germplasm, thus broadening the genetic diversity available for breeding. AB-QTL strategy was initially developed and tested in tomato, and has been adapted for use in other crops including rice, maize, wheat, pepper, barley, and bean. Once favorable QTL alleles are detected, only a few additional marker-assisted generations are required to generate near isogenic lines (NILs) or introgression lines (ILs) that can be field tested in order to confirm the QTL effect and subsequently used for variety development.

Isogenic lines in which favorable QTL alleles have been fixed can be generated by systematic backcrossing and introgressing of marker-defined donor segments in the recurrent parent background. These isogenic lines are referred to as near isogenic lines (NILs), introgression lines (ILs), backcross inbred lines (BILs), backcross recombinant inbred lines (BCRIL), recombinant chromosome substitution lines (RCSLs), chromosome segment substitution lines (CSSLs), and stepped aligned inbred recombinant strains (STAIRSs). An introgression line in plant molecular biology is a line of a crop species that contains genetic material derived from a similar species. ILs represent NILs with relatively large average introgression length, while BILs and BCRILs are backcross populations generally containing multiple donor introgressions per line. As used herein, the term "introgression lines or ILs" refers to plant lines containing a single marker defined homozygous donor segment, and the term "pre-ILs" refers to lines which still contain multiple homozygous and/or heterozygous donor segments.

To enhance the rate of progress of introgression breeding, a genetic infrastructure of exotic libraries can be developed. Such an exotic library comprises a set of introgression lines, each of which has a single, possibly homozygous, marker-defined chromosomal segment that originates from a donor exotic parent, in an otherwise homogenous elite genetic background, so that the entire donor genome would be represented in a set of introgression lines. A collection of such introgression lines is referred as libraries of introgression lines or IL libraries (ILLs). The lines of an ILL cover usually the complete genome of the donor, or the part of interest. Introgression lines allow the study of quantitative trait loci, but also the creation of new varieties by introducing exotic traits. High resolution mapping of QTL using ILLs enable breeders to assess whether the effect on the phenotype is due to a single QTL or to several tightly linked QTL affecting the same trait. In addition, sub-ILs can be developed to discover molecular markers which are more tightly linked to the QTL of interest, which can be used for marker-assisted breeding (MAB). Multiple introgression lines can be developed when the introgression of a single QTL is not sufficient to result in a substantial improvement in agriculturally important traits (Gur and Zamir, Unused natural variation can lift yield barriers in plant breeding, 2004, *PLoS Biol.*; 2(10):e245).

Plant Transformation

In some embodiments, the present invention provides transformed sweet corn plants or parts thereof that have been transformed so that its genetic material contains one or more transgenes, preferably operably linked to one or more regulatory elements. Also, the invention provides methods for producing a sweet corn plant containing in its genetic material one or more transgenes, preferably operably linked to one or more regulatory elements, by crossing transformed sweet corn plants with a second plant of another sweet corn, so that the genetic material of the progeny that results from the cross contains the transgene(s), preferably operably linked to one or more regulatory elements. The invention also provides methods for producing a sweet corn plant that contains in its genetic material one or more transgene(s), wherein the method comprises crossing a sweet corn with a second plant of another sweet corn which contains one or more transgene(s) operably linked to one or more regulatory element(s) so that the genetic material of the progeny that results from the cross contains the transgene(s) operably linked to one or more regulatory element(s). Transgenic sweet corn plants, or parts thereof produced by the method are in the scope of the present invention.

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Such foreign additional and/or modified genes are referred to herein collectively as "transgenes." Over the last fifteen to twenty years several methods for producing transgenic plants have been developed, and the present invention, in particular embodiments, also relates to transformed versions of the claimed sweet corn hybrid plant HMX4366YS and/or HMX4370BS.

Numerous methods for plant transformation have been developed, including biological and physical, plant transformation protocols. See, for example, Miki et al., "Procedures for Introducing Foreign DNA into Plants" in *Methods in Plant Molecular Biology and Biotechnology*, Glick B. R. and Thompson, J. E. Eds. (CRC Press, Inc., Boca Raton, 1993) pages 67-88. In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, Glick B. R. and Thompson, J. E. Eds. (CRC Press, Inc., Boca Raton, 1993) pages 89-119.

i *Agrobacterium*-Mediated Transformation

One method for introducing an expression vector into plants is based on the natural transformation system of *Agrobacterium*. See, for example, Horsch et al., *Science* 227:1229 (1985), Jefferson et al., *Embo J.* 3901-390764, (1987), Diant, et al., *Molecular Breeding*, 3:1, 75-86 (1997), Valles et al., *Pl. Cell. Rep.* 145-148:13 (1984). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant Sci.* 10:1 (1991). Descriptions of *Agrobacterium* vector systems and methods for *Agrobacterium*-mediated gene transfer are provided by Gruber et al., supra, Miki et al., supra, and Moloney et al., *Plant Cell Reports* 8:238 (1989). See also, U.S. Pat. No. 5,591,616 issued Jan. 7, 1997.

ii. Direct Gene Transfer

Despite the fact the host range for *Agrobacterium*-mediated transformation is broad, some major cereal crop species and gymnosperms have generally been recalcitrant to this mode of gene transfer, even though some success has been achieved in rice and corn. Hiei et al., *The Plant Journal* 6:271-282 (1994) and U.S. Pat. No. 5,591,616 issued Jan. 7, 1997. Several methods of plant transformation, collectively referred to as direct gene transfer, have been developed as an alternative to *Agrobacterium*-mediated transformation.

A generally applicable method of plant transformation is microprojectile-mediated transformation wherein DNA is carried on the surface of microprojectiles measuring 1 to 4 micron. The expression vector is introduced into plant tissues with a biolistic device that accelerates the microprojectiles to speeds of 300 to 600 m/s which is sufficient to penetrate plant cell walls and membranes. Russell, D. R., et al., *Pl. Cell. Rep.*, 12, 165-169 (1993); Aragao, F. J. L., et al., *Plant Mol. Biol.*, 20, 357-359 (1992); Aragao, *Theor. Appl. Genet.*, 93:142-150 (1996); Kim, J.; Minamikawa, T., Plant Science, 117:131-138 (1996); Sanford et al., *Part. Sci. Technol.* 5:27 (1987), Sanford, J. C., *Trends Biotech.* 6:299 (1988), Klein et al., *BioTechnology* 6:559-563 (1988), Sanford, J. C., *Physiol Plant* 7:206 (1990), Klein et al., *BioTechnology* 10:268 (1992). Gray et al., *Plant Cell Tissue and Organ Culture.* 1994, 37:2, 179-184.

Another method for physical delivery of DNA to plants is sonication of target cells. Zhang et al., *BioTechnology* 9:996 (1991). Alternatively, liposome and spheroplast fusion have been used to introduce expression vectors into plants. Deshayes et al., *EMBO J.*, 4:2731 (1985), Christou et al., *Proc Natl. Acad. Sci. U.S.A.* 84:3962 (1987). Direct uptake of DNA into protoplasts using $CaCl_2$ precipitation, polyvinyl alcohol or poly-L-ornithine has also been reported. Hain et al., *Mol. Gen. Genet.* 199:161 (1985) and Draper et al., *Plant Cell Physiol.* 23:451 (1982). Electroporation of protoplasts and whole cells and tissues have also been described. D'Halluin et al., *Plant Cell* 4:1495-1505 (1992) and Spencer et al., *Plant Mol. Biol.* 24:51-61 (1994).

Any DNA sequence(s), whether from a different species or from the same species that is inserted into the genome using transformation is referred to herein collectively as "transgenes". In some embodiments of the invention, a transformed variant of sweet corn hybrid HMX4366YS and/or HMX4370BS and/or HMX5388YS may contain at least one transgene but could contain at least 1, 2, 3, 4, 5, 6, 7, 8, 9, or 10 transgenes. In another embodiment of the invention, a transformed variant of the another sweet corn plant used as the donor line may contain at least one transgene but could contain at least 1, 2, 3, 4, 5, 6, 7, 8, 9, or 10 transgenes.

Following transformation of sweet corn target tissues, expression of the above-described selectable marker genes allows for preferential selection of transformed cells, tissues and/or plants, using regeneration and selection methods now well known in the art.

The foregoing methods for transformation would typically be used for producing a transgenic inbred line or a transgenic hybrid plant. The transgenic inbred line could then be crossed, with another (non-transformed or transformed) inbred line, in order to produce a new transgenic inbred line or plant. Alternatively, a genetic trait which has been engineered into a particular sweet corn plant using the foregoing transformation techniques could be moved into another sweet corn plant using traditional backcrossing techniques that are well known in the plant breeding arts. For example, a backcrossing approach could be used to move an engineered trait from a public, non-elite inbred line into an elite inbred line, or from an inbred line containing a foreign gene in its genome into an inbred line or lines which do not contain that gene. As used herein, "crossing" can refer to a simple X by Y cross, or the process of backcrossing, depending on the context.

iii Selection

For efficient plant transformation, a selection method must be employed such that whole plants are regenerated from a single transformed cell and every cell of the transformed plant carries the DNA of interest. These methods can employ positive selection, whereby a foreign gene is supplied to a plant cell that allows it to utilize a substrate present in the medium that it otherwise could not use, such as mannose or xylose (for example, refer U.S. Pat. No. 5,767,378; U.S. Pat. No. 5,994,629). More typically, however, negative selection is used because it is more efficient, utilizing selective agents such as herbicides or antibiotics that either kill or inhibit the growth of non-transformed plant cells and reducing the possibility of chimeras. Resistance genes that are effective against negative selective agents are provided on the introduced foreign DNA used for the plant transformation. For example, one of the most popular selective agents used is the antibiotic kanamycin, together with the resistance gene neomycin phosphotransferase (nptII), which confers resistance to kanamycin and related antibiotics (see, for example, Messing & Vierra, *Gene* 19: 259-268 (1982); Bevan et al., *Nature* 304:184-187 (1983)). However, many different antibiotics and antibiotic resistance genes can be used for transformation purposes (refer U.S. Pat. No. 5,034,322, U.S. Pat. No. 6,174,724 and U.S. Pat. No. 6,255,560). In addition, several herbicides and herbicide resistance genes have been used for transformation purposes, including the bar gene, which confers resistance to the herbicide phosphinothricin (White et al., *Nucl Acids Res* 18: 1062 (1990), Spencer et al., *Theor Appl Genet* 79: 625-631(1990), U.S. Pat. No. 4,795,855, U.S. Pat. No. 5,378,824 and U.S. Pat. No. 6,107,549). In addition, the dhfr gene, which confers resistance to the anticancer agent methotrexate, has been used for selection (Bourouis et al., *EMBO J.* 2(7): 1099-1104 (1983).

Additional selectable marker genes of bacterial origin that confer resistance to antibiotics include gentamycin acetyl transferase, streptomycin phosphotransferase, and aminoglycoside-3'-adenyl transferase, the bleomycin resistance determinant. Hayford et al., *Plant Physiol.* 86:1216 (1988), Jones et al., *Mol. Gen. Genet.*, 210:86 (1987), Svab et al., *Plant Mol. Biol.* 14:197 (1990), Hille et al., *Plant Mol. Biol.* 7:171 (1986). Other selectable marker genes confer resistance to herbicides such as glyphosate, glufosinate or bromoxynil. Comai et al., *Nature* 317:741-744 (1985), Gordon-Kamm et al., *Plant Cell* 2:603-618 (1990) and Stalker et al., *Science* 242:419-423 (1988).

Other selectable marker genes for plant transformation are not of bacterial origin. These genes include, for example, mouse dihydrofolate reductase, plant 5-enolpyruvylshikimate-3-phosphate synthase and plant acetolactate synthase. Eichholtz et al., *Somatic Cell Mol. Genet.* 13:67 (1987), Shah et al., *Science* 233:478 (1986), Charest et al., *Plant Cell Rep.* 8:643 (1990).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include beta-glucuronidase (GUS, beta-galactosidase, luciferase and chloramphenicol acetyltransferase. Jefferson, R. A., *Plant Mol. Biol. Rep.* 5:387 (1987), Teeri et al., *EMBO J.* 8:343 (1989), Koncz et al., *Proc. Natl. Acad.* Sci U.S.A. 84:131 (1987), DeBlock et al., *EMBO J.* 3:1681 (1984), Valles et al., *Plant Cell Report* 3:3-4 145-148 (1994), Shetty et al., *Food Biotechnology* 11:2 111-128 (1997)

In vivo methods for visualizing GUS activity that do not require destruction of plant tissue are also available. However, these in vivo methods for visualizing GUS activity have not proven useful for recovery of transformed cells because of low sensitivity, high fluorescent backgrounds and limitations associated with the use of luciferase genes as selectable markers. A gene encoding Green Fluorescent Protein (GFP) has been utilized as a marker for gene expression in prokaryotic and eukaryotic cells. Chalfie et al., *Science* 263:802 (1994). GFP and mutants of GFP may be used as screenable markers.

iv Expression vectors

Genes can be introduced in a site directed fashion using homologous recombination. Homologous recombination permits site-specific modifications in endogenous genes and thus inherited or acquired mutations may be corrected, and/or novel alterations may be engineered into the genome. Homologous recombination and site-directed integration in plants are discussed in, for example, U.S. Pat. Nos. 5,451, 513; 5,501,967 and 5,527,695.

The expression control elements used to regulate the expression of a given protein can either be the expression control element that is normally found associated with the coding sequence (homologous expression element) or can be a heterologous expression control element. A variety of homologous and heterologous expression control elements are known in the art and can readily be used to make expression units for use in the present invention. Transcription initiation regions, for example, can include any of the various opine initiation regions, such as octopine, mannopine, nopaline and the like that are found in the Ti plasmids of *Agrobacterium tumefaciens*. Alternatively, plant viral promoters can also be used, such as the cauliflower mosaic virus 19S and 35S promoters (CaMV 19S and CaMV 35S promoters, respectively) to control gene expression in a plant (U.S. Pat. Nos. 5,352,605; 5,530,196 and 5,858,742 for example). Enhancer sequences derived from the CaMV can also be utilized (U.S. Pat. Nos. 5,164,316; 5,196,525; 5,322, 938; 5,530,196; 5,352,605; 5,359,142; and 5,858,742 for example). Lastly, plant promoters such as prolifera promoter, fruit specific promoters, Ap3 promoter, heat shock promoters, seed specific promoters, etc. can also be used.

Either a gamete-specific promoter, a constitutive promoter (such as the CaMV or Nos promoter), an organ-specific promoter (such as the E8 promoter from tomato), or an inducible promoter is typically ligated to the protein or antisense encoding region using standard techniques known in the art. The expression unit may be further optimized by employing supplemental elements such as transcription terminators and/or enhancer elements.

Thus, for expression in plants, the expression units will typically contain, in addition to the protein sequence, a plant promoter region, a transcription initiation site and a transcription termination sequence. Unique restriction enzyme sites at the 5' and 3' ends of the expression unit are typically included to allow for easy insertion into a pre-existing vector.

In the construction of heterologous promoter/structural gene or antisense combinations, the promoter is preferably positioned about the same distance from the heterologous transcription start site as it is from the transcription start site in its natural setting. As is known in the art, however, some variation in this distance can be accommodated without loss of promoter function.

In addition to a promoter sequence, the expression cassette can also contain a transcription termination region downstream of the structural gene to provide for efficient termination. The termination region may be obtained from the same gene as the promoter sequence or may be obtained from different genes. If the mRNA encoded by the structural gene is to be efficiently processed, DNA sequences which direct polyadenylation of the RNA are also commonly added to the vector construct. Polyadenylation sequences include, but are not limited to the *Agrobacterium* octopine synthase signal (Gielen et al., *EMBO J* 3:835-846 (1984)) or the nopaline synthase signal (Depicker et al., *Mol. and Appl. Genet.* 1:561-573 (1982)). The resulting expression unit is ligated into or otherwise constructed to be included in a vector that is appropriate for higher plant transformation. One or more expression units may be included in the same vector. The vector will typically contain a selectable marker gene expression unit by which transformed plant cells can be identified in culture. Usually, the marker gene will encode resistance to an antibiotic, such as G418, hygromycin, bleomycin, kanamycin, or gentamicin or to an herbicide, such as glyphosate (Round-Up) or glufosinate (BASTA) or atrazine. Replication sequences, of bacterial or viral origin, are generally also included to allow the vector to be cloned in a bacterial or phage host; preferably a broad host range for prokaryotic origin of replication is included. A selectable marker for bacteria may also be included to allow selection of bacterial cells bearing the desired construct. Suitable prokaryotic selectable markers include resistance to antibiotics such as ampicillin, kanamycin or tetracycline. Other DNA sequences encoding additional functions may also be present in the vector, as is known in the art. For instance, in the case of *Agrobacterium* transformations, T-DNA sequences will also be included for subsequent transfer to plant chromosomes.

To introduce a desired gene or set of genes by conventional methods requires a sexual cross between two lines, and then repeated back-crossing between hybrid offspring and one of the parents until a plant with the desired characteristics is obtained. This process, however, is restricted to plants that can sexually hybridize, and genes in addition to the desired gene will be transferred.

Recombinant DNA techniques allow plant researchers to circumvent these limitations by enabling plant geneticists to identify and clone specific genes for desirable traits, such as improved fatty acid composition, and to introduce these genes into already useful varieties of plants. Once the foreign genes have been introduced into a plant, that plant can then be used in conventional plant breeding schemes (e.g., pedigree breeding, single-seed-descent breeding schemes, reciprocal recurrent selection) to produce progeny which also contain the gene of interest.

v Promoters

Genes included in expression vectors must be driven by nucleotide sequence comprising a regulatory element, for example, a promoter. Several types of promoters are now well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain organs, such as leaves, roots, seeds and tissues such as fibers, xylem vessels, tracheids, or sclerenchyma. Such promoters are referred to as "tissue-preferred". Promoters which initiate transcription only in certain tissue are referred to as "tissue-specific". A "cell type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter is a promoter which is active under most environmental conditions.

A) Inducible Promoters

An inducible promoter is operably linked to a gene for expression in sweet corn. Optionally, the inducible promoter is operably linked to a nucleotide sequence encoding a signal sequence which is operably linked to a gene for expression in sweet corn. With an inducible promoter the rate of transcription increases in response to an inducing agent.

Any inducible promoter can be used in the instant invention. See Ward et al., *Plant Mol. Biol.* 22:361-366 (1993). Exemplary inducible promoters include, but are not limited to, that from the ACEI system which responds to copper (Mett et al., *PNAS* 90:4567-4571 (1993)); In2 gene from maize which responds to benzenesulfonamide herbicide safeners (Gatz et al., *Mol. Gen. Genetics* 243:32-38 (1994)) or Tet repressor from Tn10 (Gatz et al., *Mol. Gen. Genetics* 227:229-237 (1991)). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone (Schena et al., *Proc. Natl. Acad. Sci. U.S.A.* 88:0421 (1991)).

B) Constitutive Promoters

A constitutive promoter is operably linked to a gene for expression in sweet corn or the constitutive promoter is operably linked to a nucleotide sequence encoding a signal sequence which is operably linked to a gene for expression in sweet corn.

Many different constitutive promoters can be utilized in the instant invention. Exemplary constitutive promoters include, but are not limited to, the promoters from plant viruses such as the 35S promoter from CaMV (Odell et al., *Nature* 313:810-812 (1985)) and the promoters from such genes as rice actin (McElroy et al., *Plant Cell* 2:163-171 (1990)); ubiquitin (Christensen et al., *Plant Mol. Biol.* 12:619-632 (1989) and Christensen et al., *Plant Mol. Biol.* 18:675-689 (1992)); pEMU (Last et al., *Theor. Appl. Genet.* 81:581-588 (1991)); MAS (Velten et al., *EMBO* 1 3:2723-2730 (1984)) and maize H3 histone (Lepetit et al., *Mol. Gen. Genetics* 231:276-285 (1992) and Atanassova et al., *Plant Journal* 2 (3): 291-300 (1992)). The ALS promoter, Xbal/Ncol fragment 5' to the *Brassica napus* ALS3 structural gene (or a nucleotide sequence similarity to said Xbal/Ncol fragment), represents a particularly useful constitutive promoter. See PCT application WO96/30530.C.

C) Tissue-Specific or Tissue-Preferred Promoters

A tissue-specific promoter is operably linked to a gene for expression in sweet corn. Optionally, the tissue-specific promoter is operably linked to a nucleotide sequence encoding a signal sequence which is operably linked to a gene for expression in sweet corn. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter, such as that from the phaseolin gene (Murai et al., *Science* 23:476-482 (1983) and Sengupta-Gopalan et al., *Proc. Natl. Acad. Sci. U.S.A.* 82:3320-3324 (1985)); a leaf-specific and light-induced promoter such as that from cab or rubisco (Simpson et al., *EMBO J.* 4(11):2723-2729 (1985) and Timko et al., *Nature* 318:579-582 (1985)); an anther-specific promoter such as that from LAT52 (Twell et al., *Mol. Gen. Genetics* 217:240-245 (1989)); a pollen-specific promoter such as that from Zm13 or a microspore-preferred promoter such as that from apg (Twell et al., *Sex. Plant Reprod.* 6:217-224 (1993)).

Signal Sequences for Targeting Proteins to Subcellular Compartments

Transport of protein produced by transgenes to a subcellular compartment such as the chloroplast, vacuole, peroxisome, glyoxysome, cell wall or mitochondrion or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example Becker et al., *Plant Mol. Biol.* 20:49 (1992), Knox, C., et al., *Plant Mol. Biol.* 9:3-17 (1987), Lerner et al., *Plant Physiol.* 91:124-129 (1989), Fontes et al., *Plant Cell* 3:483-496 (1991), Matsuoka et al., *Proc. Natl. Acad. Sci.* 88:834 (1991), Gould et al., *J. Cell. Biol.* 108:1657 (1989), Creissen et al., *Plant J.* 2:129 (1991), Kalderon, et al., *Cell* 39:499-509 (1984), Stiefel, et al., *Plant Cell* 2:785-793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, *Anal. Biochem.* 114:92-6 (1981).

According to a one embodiment, the transgenic plant provided for commercial production of foreign protein is a sweet corn plant. In another preferred embodiment, the biomass of interest is seed or cob. For the relatively small number of transgenic plants that show higher levels of expression, a genetic map can be generated, primarily via conventional RFLP, PCR and SSR analysis, which identifies the approximate chromosomal location of the integrated DNA molecule. For exemplary methodologies in this regard, see Glick and Thompson, *Methods in Plant Molecular Biology and Biotechnology*, Glick and Thompson Eds., CRC Press, Boca Raton 269:284 (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

Examples of Genes that Confer Resistance to Pests or Disease and that Encode:

A. Plant disease resistance genes. Plant defenses are often activated by specific interaction between the product of a disease resistance gene (R) in the plant and the product of a corresponding avirulence (Avr) gene in the pathogen. A plant variety can be transformed with one or more cloned resistance gene to engineer plants that are resistant to specific pathogen strains. See, for example Jones et al., *Science* 266:789 (1994) (cloning of the tomato Cf-9 gene for resistance to *Cladosporium fulvum*); Martin et al., *Science* 262:1432 (1993) (tomato Pto gene for resistance to *Pseudomonas syringae* pv. tomato encodes a protein kinase); Mindrinos et al., *Cell* 78:1089 (1994) (*Arabidopsis* RSP2 gene for resistance to *Pseudomonas syringae*).

B. A *Bacillus thuringiensis* protein, a derivative thereof or a synthetic polypeptide modeled thereon. See, for example, Geiser et al., *Gene* 48:109 (1986), who disclose the cloning and nucleotide sequence of a Bt alpha-endotoxin gene. Moreover, DNA molecules encoding alpha-endotoxin genes can be purchased from American Type Culture Collection, Manassas, Va., for example, under ATCC Accession Nos. 40098, 67136, 31995 and 31998.

C. A lectin. See, for example, the disclosure by Van Damme et al., *Plant Molec. Biol.* 24:25 (1994), who disclose the nucleotide sequences of several *Clivia miniata* mannose-binding lectin genes.

D. A vitamin-binding protein such as avidin. See PCT application US93/06487. The application teaches the use of avidin and avidin homologues as larvicides against insect pests.

E. An enzyme inhibitor, for example, a protease or proteinase inhibitor or an amylase inhibitor. See, for example, Abe et al., *J. Biol. Chem.* 262:16793 (1987) (nucleotide sequence of rice cysteine proteinase inhibitor), Huub et al., *Plant Molec. Biol.* 21:985 (1993) (nucleotide sequence of cDNA encoding tobacco proteinase inhibitor I), Sumitani et al., *Biosci. Biotech. Biochem.* 57:1243 (1993) (nucleotide sequence of *Streptomyces nitrosporeus* alpha-amylase inhibitor).

F. An insect-specific hormone or pheromone such as an ecdysteroid and juvenile hormone, a variant thereof, a mimetic based thereon, or an antagonist or agonist thereof. See, for example, the disclosure by Hammock et al., *Nature* 344:458 (1990), of baculovirus expression of cloned juvenile hormone esterase, an inactivator of juvenile hormone.

G. An insect-specific peptide or neuropeptide which, upon expression, disrupts the physiology of the affected pest. Pratt et al., *Biochem. Biophys. Res. Comm.* 163:1243 (1989) (an allostatin is identified in *Diploptera puntata*). See also U.S. Pat. No. 5,266,317 to Tomalski et al., who disclose genes encoding insect-specific, paralytic neurotoxins.

H. An insect-specific venom produced in nature by a snake, a wasp, etc. For example, see Pang et al., *Gene* 116:165 (1992), for disclosure of heterologous expression in plants of a gene coding for a scorpion insectotoxic peptide.

I. An enzyme responsible for a hyper-accumulation of a monoterpene, a sesquiterpene, a steroid, a hydroxamic acid, a phenylpropanoid derivative or another non-protein molecule with insecticidal activity.

J. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., *Insect Biochem. Molec. Biol.* 23:691 (1993), who teach the nucleotide sequence of a cDNA encoding tobacco hornworm chitinase, and Kawalleck et al., *Plant Molec. Biol.* 21:673 (1993), who provide the nucleotide sequence of the parsley ubi4-2 polyubiquitin gene.

K. A molecule that stimulates signal transduction. For example, see the disclosure by Botella et al., *Plant Molec. Biol.* 24:757 (1994), of nucleotide sequences for mung bean calmodulin cDNA clones, and Griess et al., *Plant Physiol.* 104:1467 (1994), who provide the nucleotide sequence of a maize calmodulin cDNA clone.

L. A hydrophobic moment peptide. See PCT application WO95/16776 (disclosure of peptide derivatives of Tachyplesin which inhibit fungal plant pathogens) and PCT application WO95/18855 (teaches synthetic antimicrobial peptides that confer disease resistance).

M. A membrane permease, a channel former or a channel blocker. For example, see the disclosure of Jaynes et al., *Plant Sci.* 89:43 (1993), of heterologous expression of a cecropin-beta, lytic peptide analog to render transgenic tobacco plants resistant to *Pseudomonas solanacearum*.

N. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., *Ann. Rev. Phytopathol.* 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus.

O. An insect-specific antibody or an immunotoxin derived therefrom. Thus, an antibody targeted to a critical metabolic function in the insect gut would inactivate an affected enzyme, killing the insect.

P. A virus-specific antibody. See, for example, Tavladoraki et al., *Nature* 366:469 (1993), who show that transgenic plants expressing recombinant antibody genes are protected from virus attack.

Q. A developmental-arrestive protein produced in nature by a pathogen or a parasite. Thus, fungal endo-alpha-1, 4-D-polygalacturonases facilitate fungal colonization and plant nutrient release by solubilizing plant cell wall homoalpha-1, 4-D-galacturonase. See Lamb et al., *BioTechnology* 10:1436 (1992). The cloning and characterization of a gene which encodes a bean endopolygalacturonase-inhibiting protein is described by Toubart et al., *Plant J.* 2:367 (1992).

R. A developmental-arrestive protein produced in nature by a plant. For example, Logemann et al., BioTechnology 10:305 (1992), have shown that transgenic plants expressing the barley ribosome-inactivating gene have an increased resistance to fungal disease.

Genes that Confer Resistance to an Herbicide, for Example:

A. An herbicide that inhibits the growing point or meristem, such as an imidazolinone or a sulfonylurea. Exemplary genes in this category code for mutant ALS and AHAS enzyme as described, for example, by Lee et al., *EMBO J.* 7:1241 (1988), and Miki et al., *Theor. Appl. Genet.* 80:449 (1990), respectively.

B. Glyphosate (resistance conferred by mutant 5-enolpyruvlshikimate-3 phosphate synthase (EPSP) and aroA genes, respectively) and other phosphono compounds such as glufosinate (phosphinothricin acetyl transferase (PAT) and *Streptomyces hygroscopicus* PAT, bar, genes), and pyridinoxy or phenoxy propionic acids and cyclohexones (ACCase inhibitor-encoding genes). See, for example, U.S. Pat. No. 4,940,835 to Shah, et al., which discloses the nucleotide sequence of a form of EPSP which can confer glyphosate resistance. A DNA molecule encoding a mutant aroA gene can be obtained under ATCC accession number 39256, and the nucleotide sequence of the mutant gene is disclosed in U.S. Pat. No. 4,769,061 to Comai. European patent application No. 0 333 033 to Kumada et al., and U.S. Pat. No. 4,975,374 to Goodman et al., disclose nucleotide sequences of glutamine synthatase genes which confer resistance to herbicides such as L-phosphinothricin. The nucleotide sequence of a PAT gene is provided in European application No. 0 242 246 to Leemans et al. DeGreef et al., BioTechnology 7:61 (1989), describe the production of transgenic plants that express chimeric bar genes coding for PAT activity. Exemplary of genes conferring resistance to phenoxy propionic acids and cyclohexones, such as sethoxydim and haloxyfop are the Acc1-S1, Acc1-S2 and Acc1-S3 genes described by Marshall et al., *Theor. Appl. Genet.* 83:435 (1992).

C. An herbicide that inhibits photosynthesis, such as a triazine (psbA and gs+ genes) or a benzonitrile (nitrilase gene). Przibilla et al., *Plant Cell* 3:169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., *Biochem. J.* 285:173 (1992).

Genes that Confer or Contribute to a Value-Added Trait, Such as:

A. Modified fatty acid metabolism, for example, by transforming a plant with an antisense gene of stearyl-ACP desaturase to increase stearic acid content of the plant. See Knutzon et al., Proc. Natl. Acad. Sci. U.S.A. 89:2624 (1992)

B. Increased resistance to high light stress such as photooxidative damages, for example by transforming a plant with a gene coding for a protein of the Early Light Induced Protein family (ELIP) as described in WO 03/074713 in the name of Biogemma.

C. Modified carbohydrate composition effected, for example, by transforming plants with a gene coding for an enzyme that alters the branching pattern of starch. See Shiroza et al., J. Bact. 170:810 (1988) (nucleotide sequence of *Streptococcus* mutants fructosyltransferase gene), Steinmetz et al., Mol. Gen. Genet. 20:220 (1985) (nucleotide sequence of *Bacillus subtilis* levansucrase gene), Pen et al., BioTechnology 10:292 (1992) (production of transgenic plants that express *Bacillus lichenifonnis*.alpha.-amylase), Elliot et al., Plant Molec. Biol. 21:515 (1993) (nucleotide sequences of tomato invertase genes), Sogaard et al., J. Biol. Chem. 268:22480 (1993) (site-directed mutagenesis of barley alpha-amylase gene), and Fisher et al., Plant Physiol. 102:1045 (1993) (maize endosperm starch branching enzyme II).

D. Increased resistance/tolerance to water stress or drought, for example, by transforming a plant to create a plant having a modified content in ABA-Water-Stress-Ripening-Induced proteins (ARS proteins) as described in WO 01/83753 in the name of Biogemma, or by transforming a plant with a nucleotide sequence coding for a phosphoenolpyruvate carboxylase as shown in WO 02/081714. The tolerance of corn to drought can also be increased by an overexpression of phosphoenolpyruvate carboxylase (PEPC-C4), obtained, for example from sorghum.

E. Increased content of cysteine and glutathione, useful in the regulation of sulfur compounds and plant resistance against various stresses such as drought, heat or cold, by transforming a plant with a gene coding for an Adenosine 5' Phosphosulfate as shown in WO 01/49855.

F. Increased nutritional quality, for example, by introducing a zein gene which genetic sequence has been modified so that its protein sequence has an increase in lysine and proline. The increased nutritional quality can also be attained by introducing into the maize plant an albumin 2S gene from sunflower that has been modified by the addition of the KDEL peptide sequence to keep and accumulate the albumin protein in the endoplasmic reticulum.

G. Decreased phytate content: 1) Introduction of a phytase-encoding gene would enhance breakdown of phytate, adding more free phosphate to the transformed plant. For example, see Van Hartingsveldt et al., Gene 127:87 (1993), for a disclosure of the nucleotide sequence of an *Aspergillus niger* phytase gene. 2) A gene could be introduced that reduced phytate content. In maize, this, for example, could be accomplished, by cloning and then reintroducing DNA associated with the single allele which is responsible for maize mutants characterized by low levels of phytic acid. See Raboy et al., Maydica 35:383 (1990).

Tissue Culture

As it is well known in the art, tissue culture of sweet corn can be used for the in vitro regeneration of sweet corn plants. Tissues cultures of various tissues of sweet corn and regeneration of plants therefrom are well known and published. By way of example, a tissue culture comprising organs has been used to produce regenerated plants as described in Girish-Chandel et al., Advances in Plant Sciences. 2000, 13: 1, 11-17, Costa et al., Plant Cell Report. 2000, 19: 3327-332, Plastira et al., Acta Horticulturae. 1997, 447, 231-234, Zagorska et al., Plant Cell Report. 1998, 17: 12 968-973, Asahura et al., Breeding Science. 1995, 45: 455-459, Chen et al., Breeding Science. 1994, 44: 3, 257-262, Patil et al., Plant and Tissue and Organ Culture. 1994, 36: 2, 255-258. It is clear from the literature that the state of the art is such that these methods of obtaining plants are routinely used and have a very high rate of success. Thus, another aspect of this invention is to provide cells which upon growth and differentiation produce sweet corn plants having the physiological and morphological characteristics of sweet corn hybrid plant HMX4366YS and/or HMX4370BS seed.

As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, seeds, leaves, stems, roots, root tips, anthers, pistils, meristematic cells, axillary buds, ovaries, seed coat, endosperm, hypocotyls, cotyledons and the like. Means for preparing and maintaining plant tissue culture are well known in the art. By way of example, a tissue culture comprising organs has been used to produce regenerated plants. U.S. Pat. Nos. 5,959,185, 5,973, 234, and 5,977,445 describe certain techniques, the disclosures of which are incorporated herein by reference.

EXAMPLES

The foregoing examples of the related art and limitations related therewith are intended to be illustrative and not exclusive. Other limitations of the related art will become apparent to those of skill in the art upon a reading of the specification.

Example 1—Development of New HMX4366YS Corn Variety

Breeding History:

Sweet corn hybrid plant HMX4366YS has superior characteristics. The female (361680) and male (361679) parents were crossed to produce hybrid (F1) seeds of HMX4366YS. The seeds of HMX4366YS can be grown to produce hybrid plants and parts thereof. The hybrid HMX4366YS can be propagated by seeds produced from crossing corn inbred line 361680 with corn inbred line 361679 or vegetatively.

The origin and breeding history of hybrid plant HMX4366YS can be summarized as follows: the line 361680 also known internally to the applicant as 360241-B was used as the female plant and crossed by pollen from 361679 also known internally to the applicant as 930277-Z (a proprietary line owned by HM.CLAUSE, Inc.). The first trial planting of this hybrid was done in Plover, Wis. in the summer of the first year. The hybrid was further trialed for two years, an example of such trial being disclosed in Tables 3 and 4.

The inbred line 361680 is a yellow shrunken-2 inbred line used as the female parent in this cross.

The inbred line 361679 is a yellow sugary-1 shrunken-2 inbred line used as the male parent in this cross.

Sweet corn hybrid plant HMX4366YS is similar to sweet corn hybrid plant Passion. Passion is a commercial variety. While similar to sweet corn hybrid plant Passion, there are significant differences including the days of flowering, from planting to 50% of plant in silk, which are 60 days for HMX4366YS while they are 64 days for Passion, the plant height is 77.2 inches for HMX4366YS while Passion is 86.9 inches, the ear height is 23.6 inches for HMX4366YS while Passion is 29.8 inches, the husk extension is 1.5 inches for HMX4366YS while Passion is 0.6 inches, the fresh kernel depth is 12.5 mm for HMX4366YS while Passion is 8.0 mm.

Also, HMX4366YS sweet corn hybrids have been shown to have a brix score of 14.6 while the brix score of Passion is 13.6.

Some of the criteria used to select the hybrid HMX4366YS as well as their inbred parent lines in various generations include: high yield, husk extension and tightness, kernel depth, kernel sweetness and ear appearance.

The sweet corn hybrid plant HMX4366YS has shown uniformity and stability for the traits, within the limits of environmental influence for the traits as described in the following Variety Descriptive Information. No variant traits have been observed or are expected for agronomical important traits in sweet corn hybrid HMX4366YS.

Sweet corn hybrid plant HMX4366YS has the following morphologic and other characteristics, as compared to Passion (based primarily on data collected in Wisconsin, all experiments done under the direct supervision of the applicant).

TABLE 1

| WHEN | TRAIT DESCRIPTION | HMX4366YS | PASSION Check |
|---|---|---|---|
| | LOCATION | Arlington, WI | Arlington, WI |
| | ROW NO. | 14-99731-36 | 14-33333-4, 33437-8 |
| | TYPE | Sweet, shrunken-2 (sh2) | Sweet, shrunken-2 (sh2) |
| | COLOR | Yellow | Yellow |
| | Region where developed in the USA | Midwest | Midwest |
| | Maturity in the Region of Best Adaptability | | |
| Flowering | from planting to 50% of plants in silk | 60 d | 64 d |
| Flowering | from planting to 50% of plants in pollen | 58 d | 62 d |
| | Plant Traits | | |
| Fresh harvest | plant height (to tassel tip); average 10 samples | 77.2 inches | 86.9 inches |
| Fresh harvest | ear height (to base of top ear node); average 10 samples | 23.6 inches | 29.8 inches |
| Fresh harvest | length of top ear internode; average 10 samples | 5.5 inches | 5.9 inches |
| Fresh harvest | anthocyanin of brace roots; absent, weak, medium, strong, very strong | Absent | absent |

TABLE 1-continued

| WHEN | TRAIT DESCRIPTION | HMX4366YS | PASSION Check |
|---|---|---|---|
| | Leaf Traits | | |
| Emergence | first leaf: anthocyanin coloration of sheath; absent, weak, medium, strong, very strong | Absent | absent |
| Emergence | first leaf: shape of tip; pointed, pointed to rounded, rounded to spatulate, spatulate | pointed to rounded | pointed to rounded |
| Flowering | Foliage intensity of green color; light, medium, dark | Medium | medium |
| Flowering | number of leaves above top ear; average 10 samples | 6.0 | 6.0 |
| Fresh harvest | width of ear node leaf; average 10 samples | 3.5 inches | 4.4 inches |
| Fresh harvest | length of ear node leaf in inches; average 10 samples | 31.9 inches | 33.5 inches |
| Flowering | angle between blade and stem (on leaf just above upper ear) 1-9<br>1 very small, 3 small +/=25*, 5 med +/=50*, 7 large +/=75*, 9 very large >=90* | 5 | 3 |
| Flowering | leaf undulation of margin of blade; absent, intermediate, strong | strong | strong |
| Flowering | degrees leaf angle (curvature)<br>absent slight recurved mod recurved strongly recurved v strongly recurved | moderatley recurved | slightly recurved |
| Flowering | sheath pubescence (1 = none to 9 = like peach fuzz) | 5 | 5 |
| Flowering | leaf: anthocyanin coloration of sheath (in middle of plant)<br>absent weak medium strong very strong | absent | absent |
| Flowering | anthocyanin coloration of internodes (in middle of plant)<br>absent weak medium strong very strong | absent | absent |
| Flowering | stem: degree of zig-zag; absent, slight, strong | slight | absent |
| | Tassel Traits | | |
| Flowering | number of primary lateral branches; very few, few, medium, many, very many | very many | many |
| Flowering | branch angle from central spike<br>1 very small, 3 small +/=25*, 5 med +/=50*, 7 large +/=75*, 9 very large >=90* | 3 | na |
| Flowering | angle between main axis and lateral branches (in lower third of tassel)<br>1 very small, 3 small +/=25*, 5 med +/=50*, 7 large +/=75*, 9 very large >=90* | 5 | 3 |
| Flowering | attitude of lateral branches (in lower third of tassel)<br>absent slight recurved mod recurved strongly recurved v strongly recurved | slightly recurved | slightly recurved |
| Flowering | Length of lateral branches; very short, short, medium, long, very long | medium | medium |
| Fresh harvest | length (from top leaf collar to tassel tip); average 10 samples | 15.2 inches | 13.4 inches |
| Flowering | Length above lowest lateral branch; average 10 samples | 15.0 inches | 14.7 inches |
| Flowering | Length above highest lateral branch; average 10 samples | 9.3 inches | 9.8 inches |
| Flowering | anther color; yellow, green, red, pink | yellow | yellow |
| Flowering | glume color; green, red | green | green |
| Flowering | bar glumes (glume bands); absent, present | absent | absent |
| Flowering | Anthocyanin coloration at base of glumes; absent, weak, medium, strong, very strong | absent | absent |
| Flowering | Anthocyanin coloration of glumes excluding base; absent, weak, medium, strong, very strong | absent | absent |
| Flowering | Anthocyanin coloration of anthers (middle third, fresh anthers)<br>absent weak medium strong very strong | absent | absent |
| Flowering | ear: anthocyanin coloration of silk; absent, present | absent | absent |
| Flowering | ear: intensity of anthocyanin coloration of silks; absent, weak, medium, strong, very strong | absent | absent |
| | Ear Traits | | |
| Flowering | (unhusked data) silk color (3 days after emergence); yellow, green, pink, red | yellow | yellow |
| Fresh harvest | (unhusked data) husk tightness (1 = very loose to 9 = very tight) | 7 | 5 |
| Fresh harvest | (unhusked data) husk extension (at harvest) in inches | 1.5 inches | 0.6 inches |
| Fresh harvest | (husked ear data) ear length; average 10 samples | 18.3 cm | 19.2 cm |
| Fresh harvest | (husked ear data) ear diameter at mid-point, average 10 samples | 4.8 cm | 4.7 cm |
| Fresh harvest | (husked ear data) number of kernel rows, average | 16-18 | 18 |
| Fresh harvest | (husked ear data) row alignment (1 to 9) | 5 | 5 |
| Fresh harvest | (husked ear data) shank length in inches | 3.5 inches | 2.5 inches |
| Fresh harvest | (husked ear data) ear taper; conical, conical cylindrical, cylindrical | conical cylindrical | conical cylindrical |

TABLE 1-continued

| WHEN | TRAIT DESCRIPTION | HMX4366YS | PASSION Check |
|---|---|---|---|
| Fresh harvest | number of kernel colors; one or two | one | one |
| Fresh harvest | intensity of yellow color; light, medium, dark | medium | medium |
| Fresh harvest | Fresh kernel width mm | 9.7 mm | 8.8 mm |
| Fresh harvest | Fresh kernel depth (mm) | 12.5 mm | 8.0 mm |
| Pre Planting | endosperm type; sh2 or su1 | sh2 | sh2 |
| Fresh harvest | Eating Quality; excellent, good, fair, poor | | |
| Fresh harvest | Brix; average 10 samples | 14.6 | 13.6 |
| | Cob Traits | | |
| Fresh harvest | diameter at mid-point; average 10 samples | 1.4 cm | 1.0 cm |
| Fresh harvest | cob color | white | white |
| | Disease Reaction Traits | | |
| Fresh harvest | Common Rust (*Puccinia sorghi*) | NA | HR Rp1D |
| Fresh harvest | Maize Dwarf Mosaic Virus (MDMV) | NA | NA |
| Fresh harvest | Stewart's Bacterial Wilt (*Pantoea stewartii*) | NA | IR |
| Fresh harvest | Northern Corn Leaf Blight (*Exserohilum turcicum*) | NA | IR |

Example 2—Development of New HMX4370BS Corn Variety

Breeding History:

Sweet corn hybrid plant HMX4370BS has superior characteristics. The female (302440) and male (302438) parents were crossed to produce hybrid (F1) seeds of HMX4370BS. The seeds of HMX4370BS can be grown to produce hybrid plants and parts thereof. The hybrid HMX4370BS can be propagated by seeds produced from crossing corn inbred line 302440 with corn inbred line 302438 or vegetatively.

The origin and breeding history of hybrid plant HMX4370BS can be summarized as follows: the line 302440 also known internally to the applicant as 360241-B was used as the female plant and crossed by pollen from 302438 also known internally to the applicant as 360471-B (a proprietary line owned by HM.CLAUSE, Inc.). The first trial planting of this hybrid was done in Plover, Wis. in the summer of the first year. The hybrid was further trialed for two years, an example of such trial being disclosed in Tables 5 and 6.

The inbred line 302440 is a yellow shrunken-2 inbred line used as the female parent in this cross.

The inbred line 302438 is a white shrunken-2 inbred line used as the male parent in this cross.

Sweet corn hybrid plant HMX4370BS is similar to sweet corn hybrid plant 274A. 274A is a commercial variety. While similar to sweet corn hybrid plant 274A, there are significant differences including the days of flowering, from planting to 50% of plants in silk, which are 56 days for HMX4370BS while they are 57 days for 274A, the plant height is 79.1 inches for HMX4370BS while 274A is 74.2 inches, the ear height is 22.6 inches for HMX4370BS while 274A is 21.0", the husk extension is 1.8 inches for HMX4370BS while 274A is 2.4 inches, the shank length for HMX4370BS is 3.0 inches while 274A is 4.7 inches, the ear length for HMX4370BS is 20.9 cm while 274A is 19.7 cm, the cob diameter for HMX4370BS is 2.6 cm while 274A is 1.4 cm, the fresh kernel depth is 12.4 mm for HMX4370BS while 274A is 12.0 mm.

Also, HMX4370BS sweet corn hybrids have been shown to have a brix score of 14.2 while the brix score of 274A is 15.6.

Some of the criteria used to select the hybrid HMX4370BS as well as their inbred parent lines in various generations include: high yield, husk tightness, ear length, ear diameter, kernel depth, and ear appearance.

The sweet corn hybrid plant HMX4370BS has shown uniformity and stability for the traits, within the limits of environmental influence for the traits as described in the following Variety Descriptive Information. No variant traits have been observed or are expected for agronomical important traits in sweet corn hybrid HMX4370BS.

Sweet corn hybrid plant HMX4370BS has the following morphologic and other characteristics, as compared to 274A (based primarily on data collected in Wisconsin, all experiments done under the direct supervision of the applicant).

TABLE 2

| WHEN | TRAIT DESCRIPTION | HMX4370BS | 274A Check |
|---|---|---|---|
| | LOCATION | Arlington, WI | Arlington, WI |
| | ROW NO. | 14-99899-04 | 14-33797-98 |
| | TYPE | Sweet, shrunken-2 (sh2) | Sweet, shrunken-2 (sh2) |
| | COLOR | Bicolor | Bicolor |
| | Region where developed in the USA | Midwest | Midwest |
| | Maturity in the Region of Best Adaptability | | |
| Flowering | from planting to 50% of plants in silk | 56 d | 57 d |
| Flowering | from planting to 50% of plants in pollen | 52 d | 54 d |
| | Plant Traits | | |
| Fresh harvest | plant height (to tassel tip); average 10 samples | 79.1" | 74.2" |
| Fresh harvest | ear height (to base of top ear node); average 10 samples | 22.6" | 21.0" |
| Fresh harvest | length of top ear internode; average 10 samples | 6.0" | 5.8" |
| Fresh harvest | anthocyanin of brace roots; absent, weak, medium, strong, very strong | absent | absent |

TABLE 2-continued

| WHEN | TRAIT DESCRIPTION | HMX4370BS | 274A Check |
|---|---|---|---|
| | Leaf Traits | | |
| Emergence | first leaf: anthocyanin coloration of sheath; absent, weak, medium, strong, very strong | absent | absent |
| Emergence | first leaf: shape of tip; pointed, pointed to rounded, rounded to spatulate, spatulate | pointed to round | rounded |
| Flowering | Foliage intensity of green color; light, medium, dark | medium | light |
| Flowering | number of leaves above top ear; average 10 samples | 6.0 | 6.0 |
| Fresh harvest | width of ear node leaf; average 10 samples | 3.7" | 3.6" |
| Fresh harvest | length of ear node leaf in inches; average 10 samples | 32.0" | 31.3" |
| Flowering | angle between blade and stem (on leaf just above upper ear) 1-9<br>1 very small, 3 small +/=25*, 5 med +/=50*, 7 large +/=75*, 9 very large >=90* | 3 | 5 |
| Flowering | leaf undulation of margin of blade; absent, intermediate, strong | strong | strong |
| Flowering | degrees leaf angle (curvature)<br><br>absent slight recurved mod recurved strongly recurved v strongly recurved | moderately recurved | strongly recurved |
| Flowering | sheath pubescence (1 = none to 9 = like peach fuzz) | 5 | 6 |
| Flowering | leaf: anthocyanin coloration of sheath (in middle of plant) absent weak medium strong very strong | absent | absent |
| Flowering | anthocyanin coloration of internodes (in middle of plant) absent weak medium strong very strong | absent | absent |
| Flowering | stem: degree of zig-zag; absent, slight, strong | slight | slight |
| | Tassel Traits | | |
| Flowering | number of primary lateral branches; very few, few, medium, many, very many | many | very many |
| Flowering | branch angle from central spike<br>1 very small, 3 small +/=25*, 5 med +/=50*, 7 large +/=75*, 9 very large >=90* | 5 | 7 |
| Flowering | angle between main axis and lateral branches (in lower third of tassel)<br>1 very small, 3 small +/=25*, 5 med +/=50*, 7 large +/=75*, 9 very large >=90* | 7 | 5 |
| Flowering | attitude of lateral branches (in lower third of tassel)<br><br>absent slight recurved mod recurved strongly recurved v strongly recurved | moderately recurved | moderately recurved |
| Flowering | Length of lateral branches; very short, short, medium, long, very long | medium | medium-long |
| Fresh harvest | length (from top leaf collar to tassel tip); average 10 samples | 16.9" | 14.7" |
| Flowering | Length above lowest lateral branch; average 10 samples | 16.0" | 14.0" |
| Flowering | Length above highest lateral branch; average 10 samples | 9.5" | 8.0" |
| Flowering | anther color; yellow, green, red, pink | yellow | green |
| Flowering | glume color; green, red | green | green |
| Flowering | bar glumes (glume bands); absent, present | absent | absent |
| Flowering | Anthocyanin coloration at base of glumes; absent, weak, medium, strong, very strong | absent | absent |
| Flowering | Anthocyanin coloration of glumes excluding base; absent, weak, medium, strong, very strong | absent | absent |
| Flowering | Anthocyanin coloration of anthers (middle third, fresh anthers)<br>absent weak medium strong very strong | absent | absent |
| Flowering | ear: anthocyanin coloration of silk; absent, present | absent | absent |
| Flowering | ear: intensity of anthocyanin coloration of silks; absent, weak, medium, strong, very strong | absent | absent |
| | Ear Traits | | |
| Flowering | (unhusked data) silk color (3 days after emergence); yellow, green, pink, red | yellow | yellow |
| Fresh harvest | (unhusked data) husk tightness (1 = very loose to 9 = very tight) | 6 | 5 |
| Fresh harvest | (unhusked data) husk extension (at harvest) in inches | 1.8" | 2.4" |
| Fresh harvest | (husked ear data) ear length; average 10 samples | 20.9 cm | 19.7 cm |
| Fresh harvest | (husked ear data) ear diameter at mid-point, average 10 samples | 4.6 cm | 4.6 cm |
| Fresh harvest | (husked ear data) number of kernel rows, average | 20 | 20 |
| Fresh harvest | (husked ear data) row alignment (1 to 9) | 5 | 4 |
| Fresh harvest | (husked ear data) shank length in inches | 3.0" | 4.7" |
| Fresh harvest | (husked ear data) ear taper; conical, conical cylindrical, cylindrical | conical cylindrical | conical cylindrical |
| Fresh harvest | number of kernel colors; one or two | two | two |
| Fresh harvest | intensity of yellow color; light, medium, dark | light | light |
| Fresh harvest | Fresh kernel width mm | 9.3 mm | 10.0 mm |

TABLE 2-continued

| WHEN | TRAIT DESCRIPTION | HMX4370BS | 274A Check |
|---|---|---|---|
| Fresh harvest | Fresh kernel depth (mm) | 12.4 mm | 12.0 mm |
| Pre Planting | endosperm type; sh2 or su1 | sh2 | sh2 |
| Fresh harvest | Eating Quality; excellent, good, fair, poor | | |
| Fresh harvest | Brix; average 10 samples | 14.2 | 15.6 |
| | Cob Traits | | |
| Fresh harvest | diameter at mid-point; average 10 samples | 2.6 cm | 1.4 cm |
| Fresh harvest | cob color | white | white |
| | Disease Reaction Traits | | |
| Fresh harvest | Common Rust (*Puccinia sorghi*) | NA | NA |
| Fresh harvest | Maize Dwarf Mosaic Virus (MDMV) | NA | NA |
| Fresh harvest | Stewart's Bacterial Wilt (*Pantoea stewartii*) | NA | NA |
| Fresh harvest | Northern Corn Leaf Blight (*Exserohilum turcicum*) | NA | NA |

Example 3—Field Trials Characteristics of Hybrid Corn Plant HMX4366YS

In tables 3 and 4, the traits and characteristics of hybrid sweet corn plant HMX4366YS are compared to the variety Passion. The data was collected during one growing season from several field locations in the United States, all experiments done under the direct supervision of the applicant.

In table 3, the first column shows the variety name, the second column shows the location of testing. The third column "PLT RATE>>" is the overall rating of the plants in the plot, on a 1 to 9 scale where 1 is for weak plants, plants with tilled and/or lodged plants, while 9 is for strong plants, uniform, with few tillers and standing. The fourth column "MRK EARS" is the number of marketable ears per plots, on a 1 to 9 scale where 1 is for plants with few marketable ears in plots and 9 is for plants with high number of marketable ears in plots. The fifth column "SNAP" is the ear removal from stalks, on a 1 to 9 scale where 1 is for plants when it is difficult to pull ear from stalk, while 9 is for an easy removal of the ear from stalk. The Sixth column "SHANK" is the length of ear shank, on a 1 to 9 scale, where 1 is for long shank remaining after ear removal from stalk and 9 is for short shank length remaining after ear removal from stalk. The seventh column "HSK CLR" is the husk leaf color on a 1 to 9 scale where 1 is for pale, light green or yellow husk leaves while 9 is for uniform dark green husk leaves. The eighth column "FLAGS" is for the appearance of flag leaves on a 1 to 9 scale where 1 is no or few short flag leaves and 9 is a high number of flag leaves, with a good length and uniform dark green color. The ninth column "HUSK P" is the husk protection of ear tip, on a 1 to 9 scale, where 1 is when the ear is exposed for 2 inches or more and 9 is when husk is extending beyond the ear tip by 3.5 inches and the hush are tightly wrapped. The tenth column "EAR SHP" is for the shape of ear, on a 1 to 9 scale, where 1 is for tapered, curved or fascinated ear while 9 is for straight and cylindrical ear. Column 11 "TYP ROW" is for the straightness and uniformity of kernels rows, on a 1 to 9 scale, where 1 is for jumbled, uneven or non-uniform kernel rows, while 9 is for straight, even and uniform rowing.

TABLE 3

| VARIETY | TRIAL LOCATION | PLT RATE | MRK EARS | SNAP | SHANK | HSK CLR | FLAGS | HUSK P | EAR SHP | TYP ROW |
|---|---|---|---|---|---|---|---|---|---|---|
| Passion (CHECK) | Bainbridge, GA | 5 | 6 | 6 | 6 | 4 | 4 | 5 | 6 | 6 |
| | Stevens Point, WI | 6 | 6 | 6 | 6 | 5 | 5 | 5 | 5 | 6 |
| | Sun Prairie, WI | 6 | 6 | 6 | 6 | 4 | 4 | 4 | 6 | 6 |
| HMX4366YS | Tracy, CA | 6 | 7 | 6 | 5 | 6 | 6 | 5 | 5 | 6 |
| | Bainbridge, GA | 6 | 7 | 6 | 6 | 6 | 6 | 6 | 6 | 6 |
| | Stevens Point, WI | 6 | 7 | 7 | 6 | 6 | 6 | 6 | 5 | 6 |
| | Tabernacle, NJ | 6 | 6 | 6 | 6 | 6 | 6 | 5 | 6 | 6 |
| | Sun Prairie, WI | 6 | 7 | 6 | 7 | 7 | 6 | 6 | 6 | 6 |

In table 4, the first column shows the variety name, the second column shows the location of testing. The third column "TIP FILL>>" is the kernel fill to tip of the ear, on a 1 to 9 scale where 1 is for up to 3 inches blanking, while 9 is for completely filled ear tip. The fourth column "E LENGTH" is the length of the ear measures in inches, measured for at least five ears per plot. The fifth column "NO ROWS" is the number of kernel rows on the ear. The Sixth column "K STYLE" is the relative size or style of kernel, on a 1 to 9 scale, where 1 is for very large, blocky rounded kernels and 9 is for small refined, even kernels. The seventh column "K COLOR" is the kernel color for yellow or white sweet corn, on a 1 to 9 scale where 1 is for dull, pale, or uneven kernel color while 9 is for kernels with an uniform, intense color, with a glossy appearance. The eighth column "KCC" is for the kernel color contrast for bicolor sweet corn, on a 1 to 9 scale where 1 is poor contrast, pale, dull, washed poor colors and 9 is for kernels having a high level of contrast, bright, with glossy intense colors. The ninth column "TENDER" is the tenderness of pericarp or the ease of bite, on a 1 to 9 scale, where 1 is for tough, firm pericarp and 9 is for very tender pericarp, without splitting in the field. The tenth column "SWEET" is for the intensity of kernel sweetness when eaten, on a 1 to 9 scale, where 1 is for bland and objectionable taste while 9 is for intensively sweet, flavorable kernels.

with tilled and/or lodged plants, while 9 is for strong plants, uniform, with few tillers and standing. The fourth column "MRK EARS" is the number of marketable ears per plots, on a 1 to 9 scale where 1 is for plants with few marketable ears in plots and 9 is for plants with high number of marketable ears in plots. The fifth column "SNAP" is the ear removal from stalks, on a 1 to 9 scale where 1 is for plants when it is difficult to pull ear from stalk, while 9 is for an easy removal of the ear from stalk. The Sixth column "SHANK" is the length of ear shank, on a 1 to 9 scale, where 1 is for long shank remaining after ear removal from stalk and 9 is for short shank length remaining after ear removal from stalk. The seventh column "HSK CLR" is the husk leaf color on a 1 to 9 scale where 1 is for pale, light green or yellow husk leaves while 9 is for uniform dark green husk

TABLE 4

| VARIETY | TRIAL LOCATION | TIP FILL | E LENGTH | NO ROWS | K STYLE | K COLOR | KCC | TENDER | SWEET |
|---|---|---|---|---|---|---|---|---|---|
| Passion (CHECK) | Bainbridge, GA | 6 | 7.0" | 16-18 | 6 | 7 | NA | 5 | 6 |
|  | Stevens Point, WI | 5 | 7.8"-8.0" | 16-18 | 6 | 6 | NA | 5 | 6 |
|  | Sun Prairie, WI | 6 | 7.2"-7.5" | 16-18 | 6 | 6 | NA | 6 | 6 |
| HMX4366YS | Tracy, CA | 6 | 8.0" | 14-18 | 6 | 6 | NA | 6 | 6 |
|  | Bainbridge, GA | 7 | 7.0"-7.5" | 14-16 | 6 | 6 | NA | 6 | 6 |
|  | Stevens Point, WI | 7 | 8.0"-8.5" | 16-18 | 6 | 5 | NA | 6 | 6 |
|  | Tabernacle, NJ | 7 | 8.0"-8.5" | 16-18 | 6 | 5 | NA | 6 | 6 |
|  | Sun Prairie, WI | 6 | 7.8"-8.2" | 16-18 | 6 | 6 | NA | 6 | 6 |

Example 4—Field Trials Characteristics of Hybrid Corn Plant HMX4370BS

In tables 5 and 6, the traits and characteristics of hybrid sweet corn plant HMX4370BS are compared to the variety 3172. The data was collected during one growing season from several field locations in the United States, all experiments done under the direct supervision of the applicant.

In table 5, the first column shows the variety name, the second column shows the location of testing. The third column "PLT RATE>>" is the overall rating of the plants in the plot, on a 1 to 9 scale where 1 is for weak plants, plants leaves. The eighth column "FLAGS" is for the appearance of flag leaves on a 1 to 9 scale where 1 is no or few short flag leaves and 9 is a high number of flag leaves, with a good length and uniform dark green color. The ninth column "HUSK P" is the husk protection of ear tip, on a 1 to 9 scale, where 1 is when the ear is exposed for 2 inches or more and 9 is when husk is extending beyond the ear tip by 3.5 inches and the hush are tightly wrapped. The tenth column "EAR SHP" is for the shape of ear, on a 1 to 9 scale, where 1 is for tapered, curved or fascinated ear while 9 is for straight and cylindrical ear. Column 11 "TYP ROW" is for the straightness and uniformity of kernels rows, on a 1 to 9 scale, where 1 is for jumbled, uneven or non-uniform kernel rows, while 9 is for straight, even and uniform rowing.

TABLE 6

| VARIETY | TRIAL LOCATION | PLT RATE | MRK EARS | SNAP | SHANK | HSK CLR | FLAGS | HUSK P | EAR SHP | TYP ROW |
|---|---|---|---|---|---|---|---|---|---|---|
| 274A (CHECK) | Brentwood, CA | 7 | 7 | 5 | 6 | 7 | 6 | 6 | 7 | 7 |
|  | Tracy, CA | 5 | 7 | 5 | 4 | 6 | 7 | 6 | 7 | 6 |
|  | Stevens Point, WI | 5 | 6 | 7 | 5 | 6 | 5 | 6 | 6 | 6 |
|  | Tabernacle, NJ | 5 | 6 | 6 | 6 | 4 | 5 | 4 | 5 | 5 |
| HMX4370BS | Brentwood, CA | 7 | 8 | 7 | 7 | 6 | 7 | 7 | 7 | 7 |
|  | Tracy, CA | 7 | 7 | 6 | 5 | 6 | 6 | 5 | 6 | 6 |
|  | Stevens Point, WI | 6 | 7 | 6 | 6 | 6 | 6 | 6 | 6 | 6 |
|  | Tabernacle, NJ | 6 | 7 | 7 | 6 | 5 | 5 | 5 | 6 | 5 |

In table 4, the first column shows the variety name, the second column shows the location of testing. The third column "TIP FILL>>" is the kernel fill to tip of the ear, on a 1 to 9 scale where 1 is for up to 3 inches blanking, while 9 is for completely filled ear tip. The fourth column "E LENGTH" is the length of the ear measures in inches, measured for at least five ears per plot. The fifth column "NO ROWS" is the number of kernel rows on the ear. The Sixth column "K STYLE" is the relative size or style of kernel, on a 1 to 9 scale, where 1 is for very large, blocky rounded kernels and 9 is for small refined, even kernels. The seventh column "K COLOR" is the kernel color for yellow or white sweet corn, on a 1 to 9 scale where 1 is for dull, pale, or uneven kernel color while 9 is for kernels with an uniform, intense color, with a glossy appearance. The eighth column "KCC" is for the kernel color contrast for bicolor sweet corn, on a 1 to 9 scale where 1 is poor contrast, pale, dull, washed poor colors and 9 is for kernels having a high level of contrast, bright, with glossy intense colors. The ninth column "TENDER" is the tenderness of pericarp or the ease of bite, on a 1 to 9 scale, where 1 is for tough, firm pericarp and 9 is for very tender pericarp, without splitting in the field. The tenth column "SWEET" is for the intensity of kernel sweetness when eaten, on a 1 to 9 scale, where 1 is for bland and objectionable taste while 9 is for intensively sweet, flavorable kernels.

TABLE 4

| VARIETY | TRIAL LOCATION | TIP FILL | E LENGTH | NO ROWS | K STYLE | K COLOR | KCC | TENDER | SWEET |
|---|---|---|---|---|---|---|---|---|---|
| 274A (CHECK) | Brentwood, CA | 7 | 8.3" | 16-18 | 6 | NA | 6 | 7 | 6 |
| | Tracy, CA | 5 | 8.0"-8.2" | 16-18 | 6 | NA | 6 | 7 | 6 |
| | Stevens Point, WI | 6 | 8.2"-8.5" | 16-20 | 6 | NA | 6 | 6 | 7 |
| | Tabernacle, NJ | 7 | 8.0"-8.2" | 16-20 | 6 | NA | 6 | 6 | 7 |
| HMX4370BS | Brentwood, CA | 7 | 8.2"-8.5" | 16-18 | 6 | NA | 7 | 7 | 7 |
| | Tracy, CA | 7 | 8.5"-9.0" | 16-18 | 6 | NA | 6 | 6 | 7 |
| | Stevens Point, WI | 7 | 8.0"-9.0" | 16-20 | 6 | NA | 6 | 6 | 7 |
| | Tabernacle, NJ | 7 | 8.5"-8.8" | 16-18 | 6 | NA | 7 | 6 | 6 |
| | Sun Prairie, WI | 7 | 8.25" | 16-20 | 6 | NA | 7 | 6 | 7 |

DEPOSIT INFORMATION

A deposit of the sweet corn seed of this invention is maintained by HM.CLAUSE, Inc. HM.CLAUSE, Sun Prairie Research & Development, 1677 Muller Road, Sun Prairie, Wis. 53590 USA. In addition, a sample of the sweet corn hybrid seed of this invention has been deposited with the National Collections of Industrial, Food and Marine Bacteria (NCIMB), 23 St Machar Drive, Aberdeen, Scotland, AB24 3RY, United Kingdom on Aug. 4, 2017.

To satisfy the enablement requirements of 35 U.S.C. 112, and to certify that the deposit of the isolated strain of the present invention meets the criteria set forth in 37 CFR 1.801-1.809, Applicants hereby make the following statements regarding the deposited sweet corn hybrid HMX4370BS (deposited as NCIMB Accession No. 42798):
1. During the pendency of this application, access to the invention will be afforded to the Commissioner upon request;
2. All restrictions on availability to the public will be irrevocably removed upon granting of the patent under conditions specified in 37 CFR 1.808;
3. The deposit will be maintained in a public repository for a period of 30 years or 5 years after the last request or for the effective life of the patent, whichever is longer;
4. A test of the viability of the biological material at the time of deposit will be conducted by the public depository under 37 CFR 1.807; and
5. The deposit will be replaced if it should ever become unavailable.

Access to this deposit will be available during the pendency of this application to persons determined by the Commissioner of Patents and Trademarks to be entitled thereto under 37 C.F.R. §1.14 and 35 U.S.C. §122. Upon allowance of any claims in this application, all restrictions on the availability to the public of the variety will be irrevocably removed by affording access to a deposit of at least 2,500 seeds of the same variety with the NCIMB.

INCORPORATION BY REFERENCE

All references, articles, publications, patents, patent publications, and patent applications cited herein are incorporated by reference in their entireties for all purposes.

However, mention of any reference, article, publication, patent, patent publication, and patent application cited herein is not, and should not be taken as an acknowledgment or any form of suggestion that they constitute valid prior art or form part of the common general knowledge in any country in the world.

What is claimed is:

1. A seed of sweet corn hybrid designated HMX4370BS, wherein a representative sample of seed of said hybrid having been deposited under NCIMB No. 42798.

2. A sweet corn plant, a part thereof, or a plant cell thereof, produced by growing the seed of claim 1, wherein a plant regenerated from the part or the plant cell has all of the physiological and morphological characteristics of the plant of HMX4370BS listed in Table 2 when grown under the same environmental conditions.

3. The sweet corn plant, a part thereof, or a plant cell of claim 2, wherein the sweet corn part is selected from the group consisting of: a leaf, a flower, an ear, and a kernel.

4. A sweet corn plant, or a part, or a plant cell thereof, wherein the plant or a plant regenerated from the part or the plant cell has all of the physiological and morphological characteristics of hybrid HMX4370BS listed in Table 2 when grown under the same environmental conditions, wherein a representative sample of seed of HMX4370BS has been deposited under NCIMB No. 42798.

5. A tissue culture of regenerable cells produced from the plant or plant part of claim 2, wherein a plant regenerated from the tissue culture has all of the physiological and morphological characteristics of hybrid HMX4370BS listed in Table 2, and wherein a representative sample of seed of said hybrid having been deposited under NCIMB No. 42798.

6. A protoplast produced from the tissue culture of claim 5, wherein a plant regenerated from the protoplast has all of the physiological and morphological characteristics of hybrid HMX4370BS listed in Table 2 when grown under the same environmental conditions.

7. A sweet corn plant regenerated from the tissue culture of claim 5, said plant having all of the physiological and morphological characteristics of hybrid HMX4370BS listed in Table 2 when grown under the same environmental conditions, wherein a representative sample of seed of said hybrid having been deposited under NCIMB No. 42798.

8. A sweet corn ear produced from the plant of claim 2.

9. A method for harvesting a sweet corn ear comprising a) growing the sweet corn plant of claim 2 to produce a sweet corn ear, and b) harvesting said sweet corn ear.

10. A sweet corn ear produced by the method of claim 9, wherein the sweet corn ear has all of the physiological and morphological characteristics of the corn ear of hybrid HMX4370BS when grown under the same environmental conditions.

11. A method for producing a sweet corn seed comprising crossing a first parent sweet corn plant with a second parent sweet corn plant and harvesting the resultant sweet corn seed, wherein said first parent sweet corn plant and/or second parent sweet corn plant is the sweet corn plant of claim 2.

12. A method for producing a sweet corn seed comprising self-pollinating the sweet corn plant of claim 2 and harvesting the resultant sweet corn seed.

13. A method of producing a sweet corn plant derived from the hybrid variety HMX4370BS, the method comprising the steps of self-pollinating the plant of claim 2 at least once to produce a progeny plant derived from the variety HMX4370BS.

14. The method of claim 13 further comprising the step of:
(a) crossing the progeny plant derived from the variety HMX4370BS with itself or a second corn plant to produce a seed of progeny plant of a subsequent generation;
(b) growing the progeny plant of the subsequent generation from the seed and crossing the progeny plant of the subsequent generation with itself or a second corn plant and (c) repeating steps (a) or (b) for at least 1 generation to produce a sweet corn plant further derived from the sweet corn hybrid variety HMX4370BS.

15. A method of producing a sweet corn plant derived from the hybrid variety HMX4370BS, the method comprising the steps of crossing the plant of claim 2 with a second corn plant to produce a progeny plant derived from the variety HMX4370BS.

16. The method of claim 15 further comprising the step of:
(a) crossing the progeny plant derived from the variety HMX4370BS with itself or a second corn plant to produce a seed of progeny plant of a subsequent generation
(b) growing the progeny plant of the subsequent generation from the seed and crossing the progeny plant of the subsequent generation with itself or a second corn plant and (c) repeating step (a) or (b) for at least 1 generation to produce a sweet corn plant further derived from the sweet corn hybrid variety HMX4370BS.

17. A method for producing a transgenic sweet corn plant, the method comprising crossing the sweet corn plant of claim 2 with a second corn plant containing a transgene, wherein the transgene of said second corn plant is integrated into the genome of the sweet corn plant progeny resulting from said cross, and wherein the transgene confers said sweet corn plant progeny with at least one trait selected from the group consisting of male sterility, male fertility, herbicide resistance, insect resistance, disease resistance, increased sweetness, increased sugar content, increased flavor, water stress tolerance, heat stress tolerance, improved ripening control, and improved salt tolerance.

18. A method for producing a transgenic sweet corn plant, the method comprising transforming at least one transgene into a sweet corn hybrid HMX4370BS plant, or a plant part or a plant cell thereof or parental line used for producing the sweet corn hybrid plant HMX4370BS, a sample seed of said hybrid having been deposited under NCIMB No. 42798, thereby producing a transgenic sweet corn plant.

19. A plant produced by the method of claim 18, wherein the plant comprises a trait conferred by the transgene in the plant, and otherwise has all of the physiological and morphological characteristics of hybrid HMX4370BS listed in Table 2 when grown under the same environmental conditions.

20. The plant of claim 2, wherein said plant further comprises a transgene.

21. The plant of claim 20 wherein the transgene confers said plant with a trait selected from the group consisting of male sterility, male fertility, herbicide resistance, insect resistance, disease resistance, increased sweetness, increased sugar content, increased flavor, water stress tolerance, heat stress tolerance, improved ripening control, and improved salt tolerance, compared to hybrid HMX4370BS when grown under the same environmental conditions.

22. The plant of claim 2 comprising at least one single locus conversion, wherein the plant comprises a trait conferred by the single locus conversion in the plant, and otherwise has all of the physiological and morphological characteristics of hybrid HMX4370BS listed in Table 2 when grown under the same environmental conditions.

23. The plant of claim 22 wherein the at least one single locus conversion confers said plant with a trait selected from the group consisting of male sterility, herbicide resistance, insect resistance, resistance for bacterial, fungal, *mycoplasma* or viral disease, improved shelf life, water-stress tolerance, delayed senescence or controlled ripening, enhanced nutritional quality such as increased sugar content or increased sweetness, increased texture, flavor and aroma, enhanced plant quality such as improved drought or salt tolerance, improved standability, enhanced plant vigor or enhanced nutritionally quality, improved husk length, protection or color, ear shape, fill, length or diameter, kernel color, refinement or depth, lodging resistance, yield and recovery, compared to hybrid HMX4370BS when grown under the same environmental conditions.

24. The plant of claim 23 wherein the at least one single locus conversion is an artificially mutated gene.

* * * * *